US011583298B2

(12) United States Patent
Robichaud et al.

(10) Patent No.: US 11,583,298 B2
(45) Date of Patent: *Feb. 21, 2023

(54) BONE RESECTION GUIDE AND METHOD

(71) Applicant: LABORATOIRES BODYCAD INC., Québec (CA)

(72) Inventors: Jean Robichaud, Quebec (CA); Florent Miquel, Quebec (CA); Geoffroy Rivet-Sabourin, Stoneham (CA); Marc Bédard, Pont-Rouge (CA)

(73) Assignee: LABORATOIRES BODYCAD INC., Québec (CA)

( * ) Notice: Subject to any disclaimer, the term of this patent is extended or adjusted under 35 U.S.C. 154(b) by 281 days.

This patent is subject to a terminal disclaimer.

(21) Appl. No.: 16/855,959

(22) Filed: Apr. 22, 2020

(65) Prior Publication Data
US 2020/0246027 A1 Aug. 6, 2020

Related U.S. Application Data

(63) Continuation of application No. 14/912,362, filed as application No. PCT/CA2014/050806 on Aug. 21, 2014, now Pat. No. 10,667,829.
(Continued)

(51) Int. Cl.
*A61B 17/17* (2006.01)
*A61B 17/15* (2006.01)
(Continued)

(52) U.S. Cl.
CPC ........ *A61B 17/1764* (2013.01); *A61B 17/157* (2013.01); *A61B 17/1604* (2013.01);
(Continued)

(58) Field of Classification Search
CPC . A61B 17/1644; A61B 17/17; A61B 17/1732; A61B 17/1739; A61B 17/1764; A61B 2017/568; A61B 2034/108
See application file for complete search history.

(56) References Cited

U.S. PATENT DOCUMENTS 5,634,927 A * 6/1997 Houston ............ A61B 17/1735
606/88
6,690,761 B2 2/2004 Lang et al.
(Continued)

FOREIGN PATENT DOCUMENTS

AU 2007202573 6/2007
AU 2007202573 A1 6/2007
(Continued)

OTHER PUBLICATIONS

International Search Report for International Application No. PCT/CA2014/050806, dated Nov. 3, 2014.
(Continued)

*Primary Examiner* — Amy R Sipp
(74) *Attorney, Agent, or Firm* — Marshall, Gerstein & Borun LLP

(57) ABSTRACT

A bone resection guide for removal of a portion of a bone of a patient. The bone resection guide includes a resecting section and a drilling section. The resecting section has a bone-facing surface, an extension engaging surface, opposed to the bone-facing surface, and at least one resecting slot extending therethrough between the bone-facing surface and the extension engaging surface. The drilling section has a connecting surface, a tool engaging surface, opposed to the connecting surface, and a plurality of guiding bores extending therethrough from the tool engaging surface to the connecting surface. The drilling section is engageable with the resecting section with the connecting surface of the drilling section facing the extension engaging surface of the resecting section and the plurality of guiding bores being aligned with the at least one resecting slot when the drilling and resecting sections are engaged and secured together.

28 Claims, 12 Drawing Sheets

Related U.S. Application Data

(60) Provisional application No. 61/868,242, filed on Aug. 21, 2013.

(51) Int. Cl.
*A61B 17/16* (2006.01)
*A61F 2/46* (2006.01)
*A61B 17/56* (2006.01)
*A61B 90/00* (2016.01)
*A61B 34/10* (2016.01)
*A61B 17/00* (2006.01)

(52) U.S. Cl.
CPC ........ *A61B 17/1735* (2013.01); *A61F 2/4603* (2013.01); *A61B 2017/00858* (2013.01); *A61B 2017/568* (2013.01); *A61B 2034/105* (2016.02); *A61B 2034/108* (2016.02); *A61B 2090/3937* (2016.02)

(56) References Cited

U.S. PATENT DOCUMENTS

| | | |
|---|---|---|
| 6,811,310 B2 | 11/2004 | Lang et al. |
| 6,904,123 B2 | 6/2005 | Lang |
| 7,050,534 B2 | 5/2006 | Lang |
| 7,058,159 B2 | 6/2006 | Lang et al. |
| 7,120,225 B2 | 10/2006 | Lang et al. |
| 7,245,697 B2 | 7/2007 | Lang |
| 7,292,674 B2 | 11/2007 | Lang |
| 7,357,057 B2 | 4/2008 | Chiang |
| 7,379,529 B2 | 5/2008 | Lang |
| 7,467,892 B2 | 12/2008 | Lang et al. |
| 7,468,075 B2 | 12/2008 | Lang et al. |
| 7,534,263 B2 | 5/2009 | Burdulis, Jr. et al. |
| 7,545,964 B2 | 6/2009 | Lang et al. |
| 7,580,504 B2 | 8/2009 | Lang et al. |
| 7,618,451 B2 | 11/2009 | Berez et al. |
| 7,634,119 B2 | 12/2009 | Tsougarakis et al. |
| 7,660,453 B2 | 2/2010 | Lang |
| 7,664,298 B2 | 2/2010 | Lang et al. |
| 7,676,023 B2 | 3/2010 | Lang |
| 7,717,956 B2 | 5/2010 | Lang |
| 7,796,791 B2 | 9/2010 | Tsougarakis et al. |
| 7,799,077 B2 | 9/2010 | Lang et al. |
| 7,840,247 B2 | 11/2010 | Liew et al. |
| 7,981,158 B2 | 7/2011 | Fitz et al. |
| 7,995,822 B2 | 8/2011 | Lang et al. |
| 8,000,441 B2 | 8/2011 | Lang et al. |
| 8,000,766 B2 | 8/2011 | Lang et al. |
| 8,031,836 B2 | 10/2011 | Lang et al. |
| 8,062,302 B2 | 11/2011 | Lang et al. |
| 8,066,708 B2 | 11/2011 | Lang et al. |
| 8,068,580 B2 | 11/2011 | Lang et al. |
| 8,073,521 B2 | 12/2011 | Liew et al. |
| 8,077,950 B2 | 12/2011 | Tsougarakis et al. |
| 8,083,745 B2 | 12/2011 | Lang et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,155,501 B2 | 4/2012 | Oda et al. |
| 8,234,097 B2 | 7/2012 | Steines et al. |
| 8,260,018 B2 | 9/2012 | Lang et al. |
| 8,290,564 B2 | 10/2012 | Lang et al. |
| 8,337,501 B2 | 12/2012 | Fitz et al. |
| 8,337,507 B2 | 12/2012 | Lang et al. |
| 8,343,218 B2 | 1/2013 | Lang et al. |
| 8,366,771 B2 | 2/2013 | Burdulis, Jr. et al. |
| 8,377,129 B2 | 2/2013 | Fitz et al. |
| 8,439,926 B2 | 5/2013 | Bojarski et al. |
| 8,460,304 B2 | 6/2013 | Fitz et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski et al. |
| 8,545,569 B2 | 10/2013 | Fitz et al. |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,588,365 B2 | 11/2013 | Lang et al. |
| 8,600,124 B2 | 12/2013 | Arnaud et al. |
| 8,617,172 B2 | 12/2013 | Fitz et al. |
| 8,617,242 B2 | 12/2013 | Philipp |
| 8,623,026 B2 | 1/2014 | Wong et al. |
| 8,625,874 B2 | 1/2014 | Lang et al. |
| 8,634,617 B2 | 1/2014 | Tsougarakis et al. |
| 8,638,998 B2 | 1/2014 | Steines et al. |
| 8,639,009 B2 | 1/2014 | Lang et al. |
| 8,641,716 B2 | 2/2014 | Fitz et al. |
| 8,649,481 B2 | 2/2014 | Lang et al. |
| 8,657,827 B2 | 2/2014 | Fitz et al. |
| 8,682,052 B2 | 3/2014 | Fitz et al. |
| 8,690,945 B2 | 4/2014 | Fitz et al. |
| 8,709,089 B2 | 4/2014 | Lang et al. |
| 8,735,773 B2 | 5/2014 | Lang |
| 8,768,028 B2 | 7/2014 | Lang et al. |
| 8,771,365 B2 | 7/2014 | Bojarski et al. |
| 8,781,191 B2 | 7/2014 | Lang et al. |
| 8,818,484 B2 | 8/2014 | Liew et al. |
| 8,882,847 B2 | 11/2014 | Burdulis, Jr. et al. |
| 8,906,107 B2 | 12/2014 | Bojarski et al. |
| 8,913,818 B2 | 12/2014 | Lang et al. |
| 8,926,706 B2 | 1/2015 | Bojarski et al. |
| 8,932,363 B2 | 1/2015 | Tsougarakis et al. |
| 8,939,917 B2 | 1/2015 | Vargas-Voracek |
| 8,945,230 B2 | 2/2015 | Lang et al. |
| 8,951,259 B2 | 2/2015 | Fitz et al. |
| 8,951,260 B2 | 2/2015 | Lang et al. |
| 8,965,075 B2 | 2/2015 | Arnaud et al. |
| 8,965,087 B2 | 2/2015 | Arnaud et al. |
| 8,965,088 B2 | 2/2015 | Tsougarakis et al. |
| 8,974,539 B2 | 3/2015 | Bojarski et al. |
| 8,998,915 B2 | 4/2015 | Fitz et al. |
| 9,020,788 B2 | 4/2015 | Lang et al. |
| 9,023,050 B2 | 5/2015 | Lang et al. |
| 9,055,953 B2 | 6/2015 | Lang et al. |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,125,673 B2 | 9/2015 | Fitz et al. |
| 9,180,015 B2 | 11/2015 | Fitz et al. |
| 9,186,161 B2 | 11/2015 | Lang et al. |
| 9,186,254 B2 | 11/2015 | Fitz et al. |
| 9,216,025 B2 | 12/2015 | Fitz et al. |
| 9,220,516 B2 | 12/2015 | Lang et al. |
| 9,220,517 B2 | 12/2015 | Lang et al. |
| 9,241,724 B2 | 1/2016 | Lang et al. |
| 9,241,725 B2 | 1/2016 | Lang et al. |
| 9,267,955 B2 | 2/2016 | Lang et al. |
| 9,275,469 B2 | 3/2016 | Lang et al. |
| 9,295,481 B2 | 3/2016 | Fitz et al. |
| 9,295,482 B2 | 3/2016 | Fitz et al. |
| 9,308,005 B2 | 4/2016 | Fitz et al. |
| 9,308,053 B2 | 4/2016 | Bojarski et al. |
| 9,308,091 B2 | 4/2016 | Lang |
| 9,314,256 B2 | 4/2016 | Fitz et al. |
| 2002/0186818 A1 | 12/2002 | Arnaud et al. |
| 2003/0055502 A1 | 3/2003 | Lang et al. |

(56) References Cited

U.S. PATENT DOCUMENTS

| | | | |
|---|---|---|---|
| 2003/0130665 A1* | 7/2003 | Pinczewski | A61B 17/154 606/88 |
| 2003/0236521 A1* | 12/2003 | Brown | A61B 17/1615 606/80 |
| 2004/0106868 A1 | 6/2004 | Liew et al. | |
| 2004/0133276 A1 | 7/2004 | Lang et al. | |
| 2005/0234465 A1 | 10/2005 | McCombs et al. | |
| 2006/0111722 A1 | 5/2006 | Bouadi | |
| 2007/0047794 A1 | 3/2007 | Lang et al. | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0233269 A1 | 10/2007 | Steines et al. | |
| 2008/0058613 A1 | 3/2008 | Lang et al. | |
| 2008/0096167 A1* | 4/2008 | Florman | A61C 3/06 433/166 |
| 2008/0097794 A1 | 4/2008 | Arnaud et al. | |
| 2008/0219412 A1 | 9/2008 | Lang | |
| 2009/0222103 A1 | 9/2009 | Fitz et al. | |
| 2009/0225958 A1 | 9/2009 | Lang | |
| 2009/0228113 A1 | 9/2009 | Lang et al. | |
| 2010/0087829 A1* | 4/2010 | Metzger | A61B 90/13 606/96 |
| 2010/0217270 A1 | 8/2010 | Polinski et al. | |
| 2010/0329530 A1 | 12/2010 | Lang et al. | |
| 2011/0029093 A1* | 2/2011 | Bojarski | A61F 2/30942 623/20.14 |
| 2011/0071645 A1 | 3/2011 | Bojarski et al. | |
| 2011/0071802 A1 | 3/2011 | Bojarski et al. | |
| 2011/0087332 A1 | 4/2011 | Bojarski et al. | |
| 2011/0144760 A1 | 6/2011 | Wong et al. | |
| 2011/0213368 A1 | 9/2011 | Fitz et al. | |
| 2011/0213374 A1 | 9/2011 | Fitz et al. | |
| 2011/0213375 A1 | 9/2011 | Sikora et al. | |
| 2011/0213377 A1 | 9/2011 | Lang et al. | |
| 2011/0213427 A1 | 9/2011 | Fitz et al. | |
| 2011/0213428 A1 | 9/2011 | Fitz et al. | |
| 2011/0213429 A1 | 9/2011 | Lang et al. | |
| 2011/0218539 A1 | 9/2011 | Fitz et al. | |
| 2011/0238073 A1 | 9/2011 | Lang et al. | |
| 2011/0313423 A1 | 12/2011 | Lang et al. | |
| 2012/0066892 A1 | 3/2012 | Lang et al. | |
| 2012/0071883 A1 | 3/2012 | Lang et al. | |
| 2012/0072185 A1 | 3/2012 | Lang et al. | |
| 2012/0116562 A1* | 5/2012 | Agnihotri | A61B 34/10 700/98 |
| 2012/0151730 A1 | 6/2012 | Fitz et al. | |
| 2012/0191205 A1 | 7/2012 | Bojarski et al. | |
| 2012/0191420 A1 | 7/2012 | Bojarski et al. | |
| 2012/0197408 A1 | 8/2012 | Lang et al. | |
| 2012/0239045 A1 | 9/2012 | Li | |
| 2012/0245699 A1 | 9/2012 | Lang et al. | |
| 2012/0277751 A1* | 11/2012 | Catanzarite | A61B 17/1764 606/88 |
| 2012/0316563 A1 | 12/2012 | Metzger et al. | |
| 2012/0323334 A1 | 12/2012 | Jones et al. | |
| 2012/0323337 A1 | 12/2012 | Parisi et al. | |
| 2013/0103363 A1 | 4/2013 | Lang et al. | |
| 2013/0110471 A1 | 5/2013 | Lang et al. | |
| 2013/0138111 A1 | 5/2013 | Aram et al. | |
| 2013/0184713 A1 | 7/2013 | Bojarski et al. | |
| 2013/0195325 A1 | 8/2013 | Lang et al. | |
| 2013/0197527 A1* | 8/2013 | Nadzadi | A61B 17/157 606/88 |
| 2013/0197870 A1 | 8/2013 | Steines et al. | |
| 2013/0211410 A1 | 8/2013 | Landes et al. | |
| 2013/0211531 A1 | 8/2013 | Steines et al. | |
| 2013/0245803 A1 | 9/2013 | Lang | |
| 2013/0253522 A1 | 9/2013 | Bojarski et al. | |
| 2013/0289570 A1 | 10/2013 | Chao | |
| 2013/0296874 A1 | 11/2013 | Chao | |
| 2013/0297031 A1 | 11/2013 | Hafez | |
| 2013/0323246 A1 | 12/2013 | Cua et al. | |
| 2013/0331850 A1 | 12/2013 | Bojarski et al. | |
| 2014/0005792 A1 | 1/2014 | Lang et al. | |
| 2014/0029814 A1 | 1/2014 | Fitz et al. | |
| 2014/0031826 A1 | 1/2014 | Bojarski et al. | |
| 2014/0066720 A1* | 3/2014 | Wilkinson | A61B 17/02 606/88 |
| 2014/0086780 A1 | 3/2014 | Miller et al. | |
| 2014/0109384 A1 | 4/2014 | Lang | |
| 2014/0115872 A1 | 5/2014 | Steines et al. | |
| 2014/0126800 A1 | 5/2014 | Lang et al. | |
| 2014/0136154 A1 | 5/2014 | Bojarski et al. | |
| 2014/0142710 A1 | 5/2014 | Lang | |
| 2014/0153810 A1 | 6/2014 | Lang et al. | |
| 2014/0163568 A1 | 6/2014 | Wong et al. | |
| 2014/0172111 A1 | 6/2014 | Lang et al. | |
| 2014/0188240 A1 | 7/2014 | Lang et al. | |
| 2014/0194996 A1 | 7/2014 | Bojarski et al. | |
| 2014/0208578 A1 | 7/2014 | Linderman et al. | |
| 2014/0222157 A1 | 8/2014 | Al Hares et al. | |
| 2014/0222390 A1 | 8/2014 | Asseln et al. | |
| 2014/0228860 A1 | 8/2014 | Steines et al. | |
| 2014/0250676 A1 | 9/2014 | Lang et al. | |
| 2014/0250677 A1 | 9/2014 | Lang | |
| 2014/0257508 A1 | 9/2014 | Bojarski et al. | |
| 2014/0259629 A1 | 9/2014 | Dion et al. | |
| 2014/0263674 A1 | 9/2014 | Cerveny | |
| 2014/0303629 A1 | 10/2014 | Lang et al. | |
| 2014/0355852 A1 | 12/2014 | Liew et al. | |
| 2014/0364857 A1 | 12/2014 | Bojarski et al. | |
| 2014/0371866 A1 | 12/2014 | Chao et al. | |
| 2015/0032215 A1 | 1/2015 | Slamin et al. | |
| 2015/0032217 A1 | 1/2015 | Bojarski et al. | |
| 2015/0057756 A1 | 2/2015 | Lang et al. | |
| 2015/0081029 A1 | 3/2015 | Bojarski et al. | |
| 2015/0093283 A1 | 4/2015 | Miller et al. | |
| 2015/0150644 A1 | 6/2015 | Lang et al. | |
| 2015/0157461 A1 | 6/2015 | Burdulis, Jr. et al. | |
| 2015/0178918 A1 | 6/2015 | Arnaud et al. | |
| 2015/0182342 A1 | 7/2015 | Hafez | |
| 2015/0216615 A1 | 8/2015 | Tsougarakis et al. | |
| 2015/0223941 A1 | 8/2015 | Lang | |
| 2015/0250552 A1 | 9/2015 | Radermacher et al. | |
| 2015/0250597 A1 | 9/2015 | Lang et al. | |
| 2016/0015465 A1 | 1/2016 | Steines et al. | |
| 2016/0038293 A1 | 2/2016 | Slamin et al. | |
| 2016/0045317 A1 | 2/2016 | Lang et al. | |
| 2016/0192949 A1* | 7/2016 | Robichaud | A61B 17/1764 606/87 |
| 2021/0353304 A1* | 11/2021 | Robichaud | A61B 90/03 |

FOREIGN PATENT DOCUMENTS

| | | |
|---|---|---|
| AU | 2011203237 | 7/2011 |
| AU | 2011203237 A1 | 7/2011 |
| AU | 2014200073 | 1/2014 |
| AU | 2014200073 A1 | 1/2014 |
| AU | 2015202416 | 5/2015 |
| AU | 2015202416 A1 | 5/2015 |
| AU | 2015203126 | 6/2015 |
| AU | 2015203126 A1 | 6/2015 |
| AU | 2015203709 | 7/2015 |
| AU | 2015203709 A1 | 7/2015 |
| AU | 2015203808 | 7/2015 |
| AU | 2015203808 A1 | 7/2015 |
| AU | 2015203823 | 7/2015 |
| AU | 2015203823 A1 | 7/2015 |
| CA | 2546965 | 6/2005 |
| CA | 2546965 A1 | 6/2005 |
| CA | 2804883 | 6/2005 |
| CA | 2804883 A1 | 6/2005 |
| CN | 102805677 | 3/2007 |
| CN | 102599960 | 7/2012 |
| CN | 102599960 A | 7/2012 |
| CN | 102805677 A | 12/2012 |
| EP | 1951136 | 8/2008 |
| EP | 1951136 A1 | 8/2008 |
| EP | 2124764 | 12/2009 |
| EP | 2124764 A1 | 12/2009 |
| EP | 2265199 | 12/2010 |
| EP | 2265199 A1 | 12/2010 |

(56) References Cited

FOREIGN PATENT DOCUMENTS

| | | |
|---|---|---|
| EP | 2303193 | 4/2011 |
| EP | 2303193 A1 | 4/2011 |
| EP | 2403434 | 1/2012 |
| EP | 2403434 A1 | 1/2012 |
| EP | 2405865 | 1/2012 |
| EP | 2405865 A2 | 1/2012 |
| EP | 2419035 | 2/2012 |
| EP | 2419035 A1 | 2/2012 |
| EP | 2512381 | 10/2012 |
| EP | 2512381 A2 | 10/2012 |
| EP | 2591756 | 5/2013 |
| EP | 2591756 A1 | 5/2013 |
| EP | 2754419 | 7/2014 |
| EP | 2754419 A2 | 7/2014 |
| WO | 02/17789 | 3/2002 |
| WO | WO-02/17789 A2 | 3/2002 |
| WO | 02/30283 | 4/2002 |
| WO | WO-02/30283 A2 | 4/2002 |
| WO | 02/96268 | 12/2002 |
| WO | 02/96284 | 12/2002 |
| WO | WO-02/96268 A2 | 12/2002 |
| WO | WO-02/96284 A1 | 12/2002 |
| WO | 2004/019256 | 3/2004 |
| WO | WO-2004/019256 A2 | 3/2004 |
| WO | 2004/049981 | 6/2004 |
| WO | WO-2004/049981 A2 | 6/2004 |
| WO | 2004/062495 | 7/2004 |
| WO | WO-2004/062495 A2 | 7/2004 |
| WO | 2004/086972 | 10/2004 |
| WO | WO-2004/086972 A2 | 10/2004 |
| WO | 2004100839 | 11/2004 |
| WO | WO-2004100839 A1 | 11/2004 |
| WO | 2005/027732 | 3/2005 |
| WO | WO-2005/027732 A2 | 3/2005 |
| WO | 2005/051239 | 6/2005 |
| WO | WO-2005/051239 A1 | 6/2005 |
| WO | 2006/034018 | 3/2006 |
| WO | WO-2006/034018 A2 | 3/2006 |
| WO | 2006/058057 | 6/2006 |
| WO | 2006/060795 | 6/2006 |
| WO | WO-2006/058057 A2 | 6/2006 |
| WO | WO-2006/060795 A1 | 6/2006 |
| WO | 2007/041375 | 4/2007 |
| WO | WO-2007/041375 A2 | 4/2007 |
| WO | 2007/062079 | 5/2007 |
| WO | WO-2007/062079 A2 | 5/2007 |
| WO | 2007/109641 | 9/2007 |
| WO | WO-2007/109641 A2 | 9/2007 |
| WO | 2010/151564 | 12/2010 |
| WO | WO-2010/151564 A1 | 12/2010 |
| WO | 2011/028624 | 3/2011 |
| WO | WO-2011/028624 A1 | 3/2011 |
| WO | 2011/056995 | 5/2011 |
| WO | WO-2011/056995 A2 | 5/2011 |
| WO | 2013/025814 | 2/2013 |
| WO | WO-2013/025814 A1 | 2/2013 |
| WO | 2013/055617 | 4/2013 |
| WO | WO-2013/055617 A1 | 4/2013 |
| WO | 2013/152341 | 10/2013 |
| WO | 2013/155500 | 10/2013 |
| WO | WO-2013/152341 A1 | 10/2013 |
| WO | WO-2013/155500 A1 | 10/2013 |
| WO | 2014/008444 | 1/2014 |
| WO | WO-2014/008444 A1 | 1/2014 |
| WO | 2014/145267 | 9/2014 |
| WO | 2014/145281 | 9/2014 |
| WO | 2014/150428 | 9/2014 |
| WO | 2014/152533 | 9/2014 |
| WO | 2014/153530 | 9/2014 |
| WO | WO-2014/145267 A1 | 9/2014 |
| WO | WO-2014/145281 A1 | 9/2014 |
| WO | WO-2014/150428 A2 | 9/2014 |
| WO | WO-2014/152533 A1 | 9/2014 |
| WO | WO-2014/153530 A1 | 9/2014 |
| WO | 2015/112566 | 7/2015 |
| WO | 2015/112570 | 7/2015 |
| WO | WO-2015/112566 A1 | 7/2015 |
| WO | WO-2015/112570 A1 | 7/2015 |
| WO | 2015/162543 | 10/2015 |
| WO | WO-2015/162543 A1 | 10/2015 |

OTHER PUBLICATIONS

Written Opinion of the International Searching Authority for International Application No. PCT/CA2014/050806, dated Nov. 3, 2014.
Supplementary European Search Report for Application No. EP14837351, dated Mar. 15, 2017.

* cited by examiner

BONE RESECTION GUIDE AND METHOD

CROSS REFERENCE TO RELATED APPLICATION

This application is a continuation of U.S. patent application Ser. No. 14/912,362, a US national phase entry of PCT patent application serial number PCT/CA2014/050806, filed on Aug. 21, 2014, designating the United States of America, which claimed the benefit under 35 U.S.C. § 119(e) of the filing date of U.S. provisional patent application No. 61/868,242 which was filed on Aug. 21, 2013. The entirety of the aforementioned applications is herein incorporated by reference.

FIELD OF THE INVENTION

The present invention relates to the field of bone resection guides. More particularly, it relates to a bone resection guide designed to perform a weakening of a bone along at least one cutting plane to allow subsequent resection of the bone. The invention also relates to a method for performing the resection of a bone using the bone resection guide.

BACKGROUND

It is known in a number of surgical procedures, to perform a resection of a portion of a bone, for example and without being limitative, to insert a prosthesis or an orthopedic implant, in a joint of a patient. To perform such resections, resection guides are commonly used to assist the surgeon.

Resection guides currently available to surgeons for performing a resection of a portion of a bone are designed such that, once the resection guide has been properly positioned and secured to the corresponding portion of the bone of the patient, the bone is cut directly using a cutting tool. However, resections performed by directly cutting the bone of a patient tend to require a long positioning procedure for the resection guide to be properly positioned and even then, in some instance, the resulting positioning may not be perfectly precise.

Moreover, known resection guides are generally not patient-specific. Therefore, before proceeding to a resection, the surgeon must perform a series of adjustments in order to adapt the resection guide to the specific patient and situation. As precision is imperative when performing a resection, when using non patient specific resection guides, the adjustment process is inevitable in order to be able to perform different types of resections on patients with different physical characteristics.

In view of the above, there is a need for an improved bone resection guide and a method for resection of a portion of a bone which would be able to overcome or at least minimize some of the above-discussed prior art concerns.

SUMMARY

According to a first general aspect, there is provided a bone resection guide for the resection of a bone of a patient. The bone resection guide comprises a body and a resection alignment guide. The body extends between a tool engaging surface and a bone-facing surface superposable to the bone of the patient and is removably securable to the bone of the patient with the bone facing surface superposed thereto. The resection alignment guide defines at least one resection plane and extends along a resection path. The resection alignment guide comprises a plurality of guiding bores extending from the tool engaging surface into at least a section of the body, along the resection path.

In an embodiment, the bone-facing surface is configured to nestingly conform to a portion of the bone of the patient.

In an embodiment, the plurality of guiding bores extend between the tool engaging surface and the bone-facing surface of the body.

In an embodiment, the body comprises a resecting section with the bone-facing surface, the resecting section including at least one resecting slot extending therethrough and along the resection path and a drilling section with the plurality of guiding bores extending therethrough. The at least one resecting slot and the plurality of guiding bores together define the resection alignment guide.

In an embodiment, the resecting section comprises a bone fastening assembly configured to secure the resecting section to the bone of the patient and the drilling section is free of bone fastening assembly.

In an embodiment, the resecting section is connected to the drilling section by at least one permanent connector with the plurality of guiding bores of the drilling section being aligned with the at least one resecting slot of the resecting section along the resection path.

In an embodiment, the at least one permanent connector is severable to disengage the drilling section from the resecting section.

In an embodiment, the resecting section is removably engageable to the drilling section. The plurality of guiding bores of the drilling section are aligned with the at least one resecting slot of the resecting section when the resecting section and the drilling section are engaged together.

In an embodiment, the bone resection guide further comprises a fastening assembly for detachably securing the resecting section and the drilling section to one another. The fastening assembly remains engaged with one of the resecting section and the drilling section when the resecting section and the drilling section are disengaged from one another.

In an embodiment, the bone resection guide further comprises an alignment assembly between a connecting surface of the drilling section opposed to the tool engaging surface and an extension engaging surface of the resecting section, opposed to the bone-facing surface.

In an embodiment, the bone-facing surface is a textured surface.

In an embodiment, the bone-facing surface comprises a plurality of protrusions with channels extending therebetween In an embodiment, a thickness of the body varies according to a depth of a section of the bone to be resected. The body is thicker in thinner sections of the bone and thinner in thicker sections of the bone.

In an embodiment, the body further comprises a hose connector having a hose receiving port, an opposed bone facing surface port, and a fluid channel extending therebetween. The hose connector is configured to allow fluid injection at the bone facing surface.

According to another general aspect, there is also provided a method for performing a resection of a portion of a bone of a patient using the above described bone resection guide. The method comprises the steps of: positioning the bone resection guide over a predetermined surface of the bone; securing the bone resection guide to the bone; weakening the bone of the patient by inserting a drilling tool in the guiding bores and drilling a plurality of holes in the bone; removing at least the section of the body of the bone resection guide comprising the plurality of guiding bores; and performing resection of the bone along the resection path.

In an embodiment, the method further comprises the preoperative steps of: generating a computer model of at least a portion of the bone of a patient on which a resection is to be performed; and conceiving the bone resection guide based on the computer model with a bone-facing surface shaped to nestingly conform to the surface of the bone of the patient on which the bone resection guide is to be positioned.

In an embodiment, the step of conceiving the bone resection guide based on the computer model comprises the sub step of determining a bone resection path and aligning the resection alignment guide with the bone resection path.

In an embodiment, the step of performing resection of the bone along the resection path is performed using one of a chisel, a manual bone saw, a bone rongeur and a bone cutter.

According to another general aspect, there is also provided a method for performing a resection of a portion of a bone of a patient. The method comprises: positioning a bone resection guide over a predetermined surface of the bone, the bone resection guide comprising a resection alignment guide with a plurality of guiding bores extending through at least a drilling section of a body of the bone resection guide and defining at least one resection plane; securing the bone resection guide to the bone; weakening the bone of the patient by inserting a drilling tool in the guiding bores and drilling a plurality of holes in the bone; removing at least the drilling section of the bone resection guide; and performing resection of the bone along the at least one resection plane.

In an embodiment, the method further comprises the preoperative steps of: generating a computer model of at least a portion of a patient bone on which a resection is to be performed; and conceiving the bone resection guide based on the computer model with a bone-facing surface shaped to nestingly conform to the surface of the bone of the patient on which the bone resection guide is to be positioned.

In an embodiment, the step of conceiving the bone resection guide based on the computer model comprises the sub step of determining a bone resection path and aligning the resection alignment guide with the bone resection path.

In an embodiment, the step of performing resection of the bone along the at least one resection plane is performed using one of a chisel, a manual bone saw, a bone rongeur and a bone cutter.

In an embodiment, the step of removing at least the drilling section of the bone resection guide comprises removing the drilling section of the bone resection guide from a resecting section of the bone resection guide to expose a resecting slot, the resecting slot being unimpeded by the guiding bores.

In an embodiment, the step of performing resection of the bone along the at least one resection plane comprises cutting the bone by displacing a cutting tool in a cutting state along the cutting slot.

In an embodiment, the step of securing the bone resection guide to the bone comprises securing a resecting section with a bone facing surface to the bone and engaging a drilling section with the resecting section.

According to a general aspect, there is provided a bone resection guide for removal of a portion of a bone of a patient. The bone resection guide comprises: a resecting section and a drilling section. The resecting section has a bone-facing surface having a bone-contacting section and an extension engaging surface, opposed to the bone-facing surface. The bone-contacting section of the bone-facing surface is removably superposable against an at least partially unresected portion of a bone of a patient and nestingly conforming thereto. The resecting section further comprises at least one resecting slot extending therethrough between the bone-facing surface and the extension engaging surface. The drilling section has a connecting surface and a tool engaging surface, opposed to the connecting surface. The drilling section comprises a plurality of guiding bores extending therethrough from the tool engaging surface to the connecting surface. The drilling section is detachably engageable to the resecting section with the connecting surface of the drilling section facing the extension engaging surface of the resecting section and the plurality of guiding bores being aligned with the at least one resecting slot when the drilling and resecting sections are engaged and secured together.

In an embodiment, at least one of the resecting section and the drilling section comprises a section fastening assembly to detachably secure the resecting section and the drilling section together. The section fastening assembly can remain engaged with the at least one of the resecting section and the drilling section when the resecting section and the drilling section are disengaged from one another.

In an embodiment, the resecting section and the drilling section are engageable together in a single configuration.

In an embodiment, the at least one resecting slot defines a resection path to create a bone resection along at least two resection planes.

In an embodiment, the at least one resecting slot defines a resection path to create a bone resection along at least one resection plane and the plurality of guiding bores and the at least one resecting slot define a resection alignment guide having a variable depth along the resection path. The portion of the bone of the patient being removed with the bone resection guide can be a bone block and the resection path can be configured to at least partially delimit the bone block to be removed from the bone of the patient, the bone block having a surface conforming substantially in shape to the at least one resection plane. A combined thickness of the drilling and resecting sections when secured together can be variable according to a depth of a section of the bone to be resected, the combined thickness being thicker for a shorter bone resection and thinner for a longer bone resection. The plurality of guiding bores can have a variable length along the resection path.

In an embodiment, the connecting face of the drilling section is superposed to the extension engaging surface of the resecting section when the drilling and resecting sections are engaged and secured together.

In an embodiment, the bone-facing surface of the resecting section has a greater surface area than the bone-contacting section thereof.

In an embodiment, the at least one resecting slot extends at least to a profile edge of the bone at at least one end thereof to be capable of performing a bone cut opened on an unresected portion of a bone surface.

In an embodiment, the at least one resecting slot extends at least to a profile edge of the bone at at least one end thereof to be capable of performing a bone cut opened at the profile edge.

In an embodiment, the resecting section comprises a bone fastening assembly to removably secure the resecting section to the bone of the patient.

According to another general aspect, there is provided a bone resection guide for removal of a portion of a bone of a patient. The bone resection guide comprises: a resecting section and a drilling section. The resecting section has a bone-facing surface and an extension engaging surface, opposed to the bone-facing surface. The resecting section further comprises at least one resecting slot extending therethrough between the bone-facing surface and the extension engaging surface. The drilling section has a connecting surface and a tool engaging surface, opposed to the connecting surface. The drilling section comprises a plurality of guiding bores extending therethrough from the tool engaging surface to the connecting surface. The drilling section is detachably engageable to the resecting section, in a single configuration, with the connecting surface of the drilling section facing the extension engaging surface of the resecting section with the plurality of guiding bores being aligned with the at least one resecting slot when the drilling and resecting sections are secured together. At least one of the resecting section and the drilling section can comprise a section fastening assembly to detachably secure the resecting section and the drilling section together.

According to still another general aspect, there is provided a bone resection guide for removal of a portion of a bone of a patient. The bone resection guide comprises: a resecting section and a drilling section. The resecting section has a bone-facing surface and an extension engaging surface, opposed to the bone-facing surface. The resecting section further comprises at least one resecting slot extending therethrough between the bone-facing surface and the extension engaging surface and defining a resection path. The drilling section has a connecting surface and a tool engaging surface, opposed to the connecting surface. The drilling section comprises a plurality of guiding bores extending therethrough from the tool engaging surface to the connecting surface. The drilling section is mounted to the resecting section with the connecting surface of the drilling section facing the extension engaging surface of the resecting section with the plurality of guiding bores being aligned with the at least one resecting slot when the drilling and resecting sections are secured together. The plurality of guiding bores and the at least one resecting slot can define a resection alignment guide having a variable depth along the resection path.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which:

FIG. 12a shows the tibia following a weakening step; FIG. 12b shows the tibia following a resection along a substantially horizontal resection plan; FIG. 12c shows the tibia following a resection along a substantially horizontal resection plan and along a substantially vertical resection plan; FIG. 12d shows the tibia after the resected portion has been removed.

DETAILED DESCRIPTION

In the following description, the same numerical references refer to similar elements. The embodiments, geometrical configurations, materials mentioned and/or dimensions shown in the figures or described in the present description are preferred embodiments only, given solely for exemplification purposes.

Moreover, although the embodiments of the bone resection guide and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, can be used for the bone resection guide, as will be briefly explained herein and as can be easily inferred herefrom by a person skilled in the art.

Figure 1:
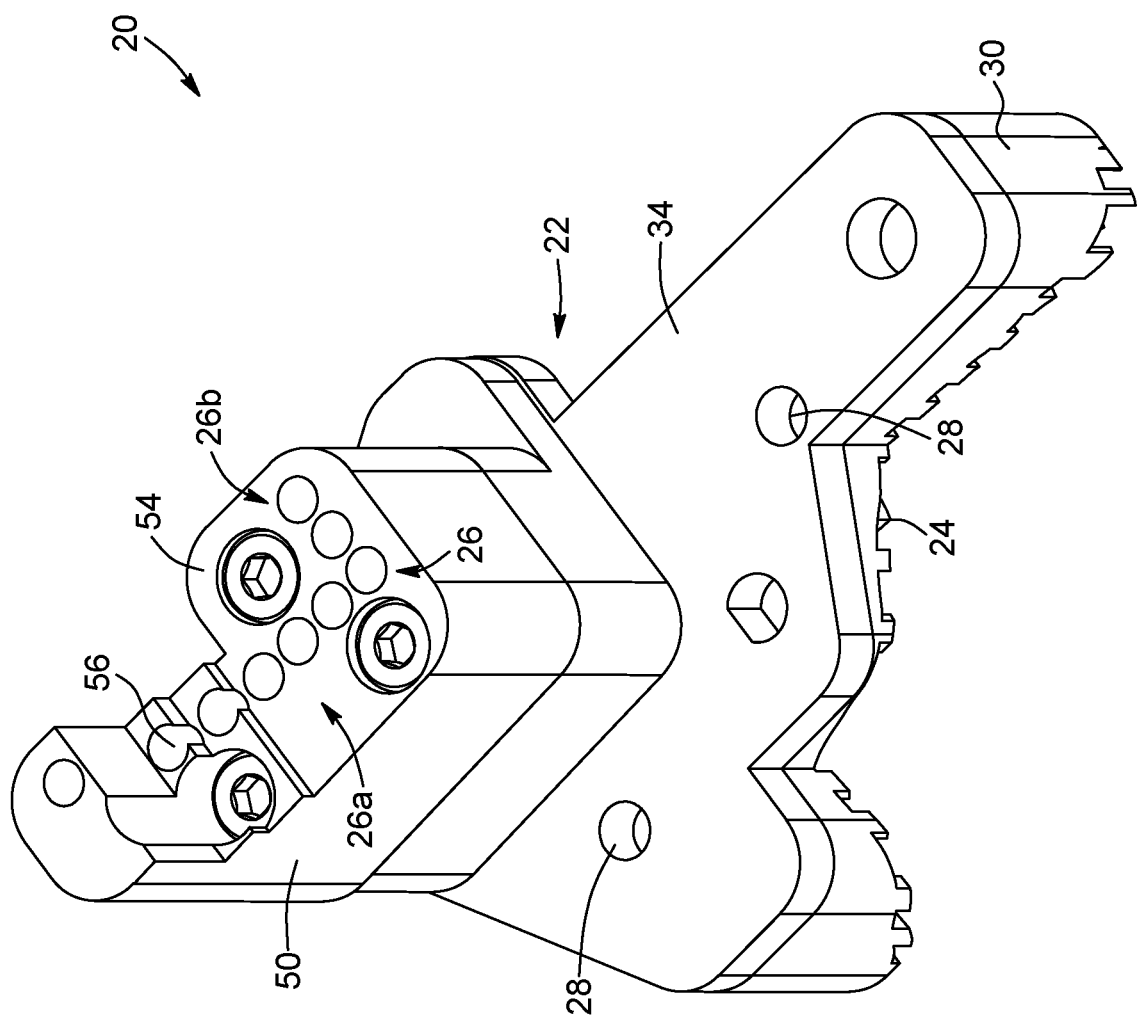
FIG. 1 is a top perspective view of a non-unitary bone resection guide according to an embodiment.
Figure 2:
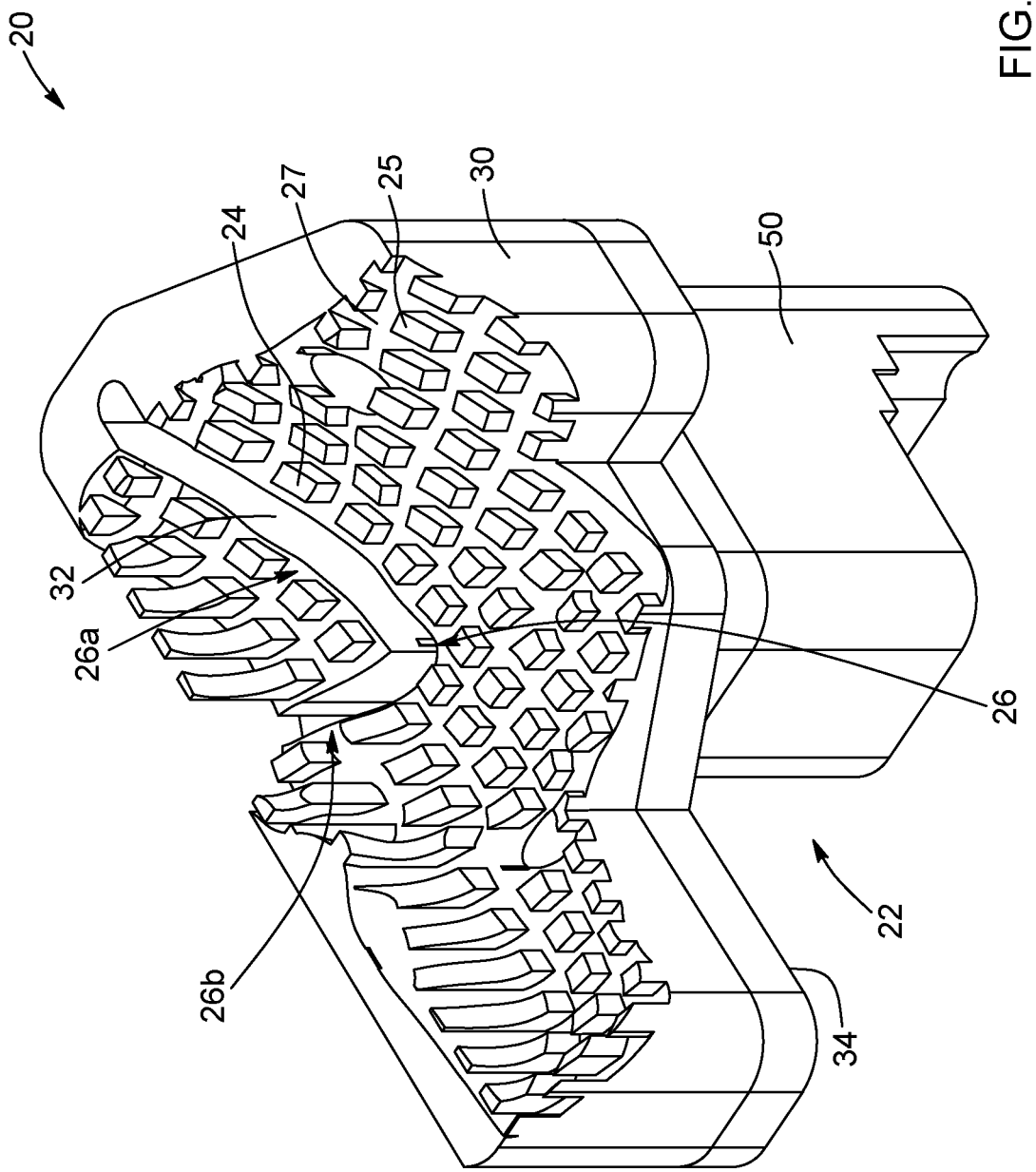
FIG. 2 is a bottom perspective view of the non-unitary bone resection guide of FIG. 1 showing a bone-facing surface thereof.
Figure 3:
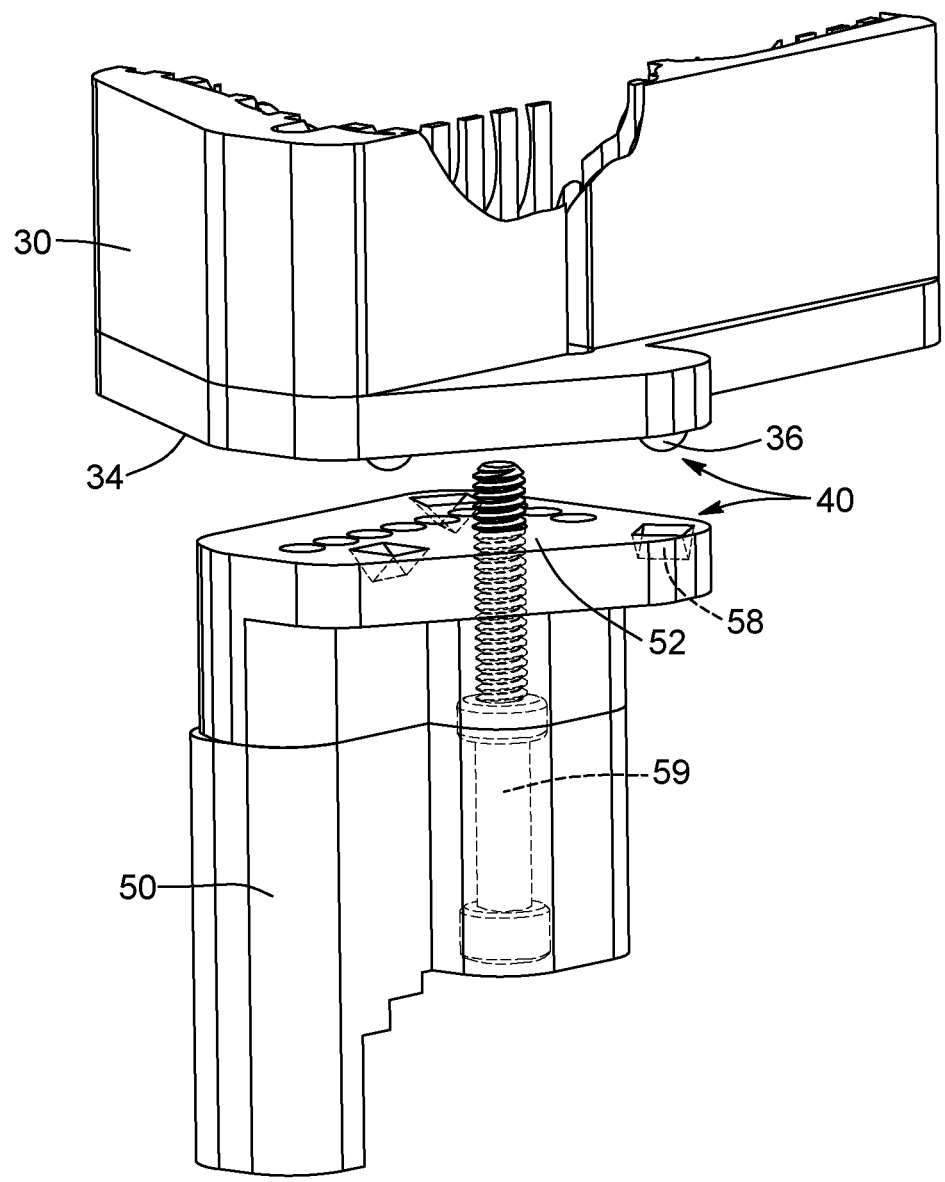
FIG. 3 is a side elevation view of the non-unitary bone resection guide of FIG. 1 wherein a resecting section and a drilling section are disengaged from one another.

Referring generally to FIGS. 1 to 3, in accordance with an embodiment, there is provided a bone resection guide 20 to be used by a surgeon to perform the resection of a portion of a bone. In the embodiment shown in the figures, the bone resection guide 20 is adapted to be detachably engaged to a tibia, to guide a resection of the upper part of the tibia. However, it is appreciated that, in alternative embodiments, the bone resection guide 20 can be designed to be detachably engaged to other suitable bones, to guide a resection of a portion of the corresponding bone. Consequently, the shape and the configuration of the bone resection guide 20 can be selected and adapted to the corresponding bone to which the bone resection guide 20 is to be engaged and can differ from the embodiment shown in the figures.

The bone resection guide 20 has a body 22 with a bone-facing surface 24. In an embodiment, the bone-facing surface 24 is designed to be complementary to a portion of a bone surface of the patient and nestingly conform to the portion of the bone surface onto which the bone resection guide 20 is to be secured. In other words, the bone-facing surface 24 is patient specific and can mate with the portion of the bone surface of the bone in a single position. As mentioned above, in an alternative embodiment, the bone resection guide 20 can be adapted to be detachably engaged to bones different than the tibia. Hence, the shape of the bone-facing surface 24 will vary in accordance with the bone to which the bone resection guide 20 is designed to be detachably engaged and the specific shape of the bone of the patient.

The body 22 of the bone resection guide 20 further comprises a resection alignment guide 26 extending therethrough. The resection alignment guide 26 defines at least one resection plane and is configured for guiding at least one resection tool, such as a drilling tool, along the at least one resection plane to perform steps of a preoperatively predetermined resection of the bone. In the embodiment shown, the resection alignment guide 26 is configured to perform a medial resection of a tibial bone and includes a substantially horizontal resection plane 26a and a substantially vertical resection plane 26b. In the embodiment shown the substantially horizontal resection plane 26a and the substantially vertical resection plane 26b of the resection alignment guide 26 form an acute angle. One skilled in the art will understand that, in alternative embodiments, the resection alignment guide 26 can be configured to perform other types of resections, according to different preoperatively predetermined resections. As mentioned above, the resections can also be directed to other bones than the tibia. The shape of the resections can vary from the embodiment shown. They can extend along one plane only or more than one plane.

The bone resection guide 20 can be made of any biocompatible material, such as metal, plastic, polymer, composite materials or the like. Each bone resection guide 20 can be manufactured by known machining methods such as, without being limitative, stereolithography methods, selective laser sintering, fused deposition modeling, milling, injection molding or the like.

Still referring to FIGS. 1 to 3, in the embodiment shown, the bone resection guide 20 is non-unitary. Therefore, the body 22 includes a resecting section 30 and a drilling section 50 removably engageable to one another, as shown in FIG. 3.

In the embodiment shown, the resecting section 30 includes the bone-facing surface 24 and is the section of the body 22 juxtaposable to the bone of the patient. More particularly, the bone-facing surface 24 is configured to nestingly conform to the portion of the bone surface onto which the resecting section 30 is to be detachably secured. The resecting section 30 further comprises an extension engaging surface 34 opposite to the bone-facing surface 24. In the embodiment shown, the extension engaging surface 34 is substantially planar but, in alternative embodiments, its shape can vary from the embodiment shown. In the embodiment shown, a resecting slot 32 extends between the bone-facing surface 24 and the extension engaging surface 34. The resecting slot 32 is part of the resection alignment guide 26, as will be described in more details below. In the embodiment shown, the bone resection guide 20 is designed to perform a unicompartemental knee arthroplasty. Thus, the resecting slot 32 is designed to perform the corresponding predetermined resection. However, the shape of the resecting slot 32 can vary from the embodiment shown. For instance and without being limitative, the resecting slot 32 can have a curve shape or a straight shape, it can include a broken line with line segments connected to or disconnected from one another, or the like.

In an embodiment, as shown in FIG. 2, the bone-facing surface 24 is textured in order to allow the proper placement of the resecting section 30 on the corresponding portion of the bone surface of the patient, even if a quantity of soft tissues, such as cartilages, remains on the bone following an anterior preparation of the bone. In other words, the bone-facing surface 24 is not a smooth surface configured to conform to the portion of the bone surface of the patient, but rather contains a plurality of cavities for receiving soft tissues that may remain on the surface of the portion of the bone. In the embodiment shown, the bone-facing surface 24 is defined by a plurality of protrusions 25 with channels 27 extending therebetween. The height and shape of the top surface of each protrusion 25 defines the bone-facing surface 24 and the empty spaces defined by the channels 27 can receive therein the above-mentioned soft tissues, thereby allowing the proper matching of the resecting section 30 on the bone and prevent undesired deviation of the bone resection guide 20 from its predetermined position on the bone, which might have been caused by the soft tissues.

Referring back to FIG. 1, there is shown that the resecting section 30 also includes a fastening assembly 28 for fastening the resecting section 30 to the bone, For example and without being limitative, in the embodiment shown, the fastening assembly includes a plurality of fastening apertures where fasteners can be inserted to secure the resecting section 30 to the bone of the patient. In an embodiment, and without being limitative, during the operative stage, the resecting section 30 is temporarily secured to the bone of the patient using screws inserted through the fastening apertures of the fastening assembly 28 and into the bone of the patient.

In the embodiment shown in FIGS. 1 and 3, the drilling section 50 is the section of the body 22 removably connectable to the extension engaging surface 34 of the resecting section 30 and extending therefrom. The drilling section 50 includes a connecting surface 52 at a first end and a tool engaging surface 54 at an opposite end. In the embodiment shown, the connecting surface 52 abuts the extension engaging surface 34 of the resecting section 30 when the drilling section 50 is secured to the resecting section 30. The tool engaging surface 54 is the opposite surface, facing away from the bone-facing surface 24 of the resecting section 30. In order to provide a suitable connection between the connecting surface 52 and the extension engaging surface 34, both surfaces are substantially complementary in shape. In the embodiment shown, the connecting surface 52 and the extension engaging surface 34 are substantially flat surfaces.

Referring to FIG. 1, there is shown that the drilling section 50 also includes a plurality of guiding bores 56 extending between the tool engaging surface 54 and the connecting surface 52, i.e. the guiding bores 56 are through holes extending therebetween. When the resecting section 30 and the drilling section 50 of the bone resection guide 20 are engaged to one another, the plurality of guiding bores 56 are disposed along the drilling section 50 to match the shape of the resecting slot 32 formed in the resecting section 30. In other words, the guiding bores 56 are aligned with the resecting slot 32 extending through the resecting section 30. Thus, the shape defined by the plurality of guiding bores 56 conforms to the shape of the resecting slot 32 and an alignment of the guiding bores 56 defines a resection path in register with the resecting slot 32 when the resecting section 30 and the drilling section 50 are engaged together. In the embodiment shown, the combination of the plurality of guiding bores 56 and the resecting slot 32 forms the resection alignment guide 26.

As shown in FIGS. 1 to 3, in the embodiment shown, the thickness of the drilling section 50 is variable and, therefore, the length of the guiding bores 56 extending therethrough is consequently also variable. As will be described in more details below, the thickness of the drilling section 50 and the resulting length of the guiding bores 56 are selected to guide the surgeon during the surgery by allowing a longer or shorter length of a drill bit of a drill to drill into the bone. In an alternative embodiment, the thickness of the drilling section 50 and the resulting length of the guiding bores 56 can be substantially uniform.

As will be understood, the alignment between the resecting section 30 and the drilling section 50 is crucial to ensure that the plurality of guiding bores 56 of the drilling section 50 are aligned with the resecting slot 32 of the resecting section 30 when the drilling section 50 is secured to the resecting section 30. In an embodiment, an alignment assembly 40 is therefore provided between the connecting surface 52 of the drilling section 50 and the extension engaging surface 34 of the resecting section 30. In the embodiment shown in FIG. 3, the alignment assembly 40 is composed of three rounded protrusions 36 extending outwardly from the extension engaging surface 34 of the resecting section 30 and three corresponding depressions 58 formed in the connecting surface 52 of the drilling section 50. In the illustrated embodiment, the depressions 58 are triangular prism in shape such that each protrusion 36 and the corresponding depressions 58 can be steadily inserted and maintained in the depressions 58, even in the presence of a certain quantity of residues therein, without causing a deviation therebetween. Thus, each one of the depressions 58 is aligned with a corresponding one of the protrusions 36 when the resecting section 30 and the drilling section 50 are detachably engaged together. The configuration of the complementary male and female members comprised in the resecting section 30 and the drilling section 50 ensures that the resecting section 30 and the drilling section 50 are engageable together in a single configuration.

One skilled in the art will understand that, in alternative embodiments, the alignment assembly 40 can present a different configuration than the one of the embodiment shown. For example and without being limitative, the protrusions 36 and corresponding depressions 58 can be inverted along the extension engaging surface 34 and the connecting surface 52 or can be configured in an alternating configuration where a surface contains at least one protrusion 36 and one depression 58. The amount of protrusions 36 and corresponding depressions 58 can also differ from the embodiment shown, given that a sufficient amount of protrusions 36 and corresponding depressions 58 is provided to maintain the alignment therebetween. In another alternative embodiment, the shape and size of the protrusions 36 and corresponding depressions 58 can differ, or a different male-female configuration can be provided.

In the embodiment shown in FIGS. 1 to 3, in order to secure the drilling section 50 to the resecting section 30, a fastener 59 is provided. In an embodiment, the fastener 59 is operative to press the connecting surface 52 of the drilling section 50 against the extension engaging surface 34 of the resecting section 30, thereby constricting the protrusions 36 of the alignment assembly 40 into the corresponding depressions 58. In an embodiment, the fastener 59 is a threaded fastener, such as a screw, extending substantially centrally through the drilling section 50 and engaging a complementary threaded bore (not shown) extending in the resecting section 30. In order to prevent the screw from being dropped by a surgeon when manipulating the components, which is undesirable as it can require the screw to be re-sterilised before it can be used again, the screw can be configured to be permanently maintained in a securing channel of the drilling section 50. In alternative embodiments, other fasteners or fastening assembly can be provided to detachably engage the resecting section 30 and the drilling section 50 together.

Figure 8:
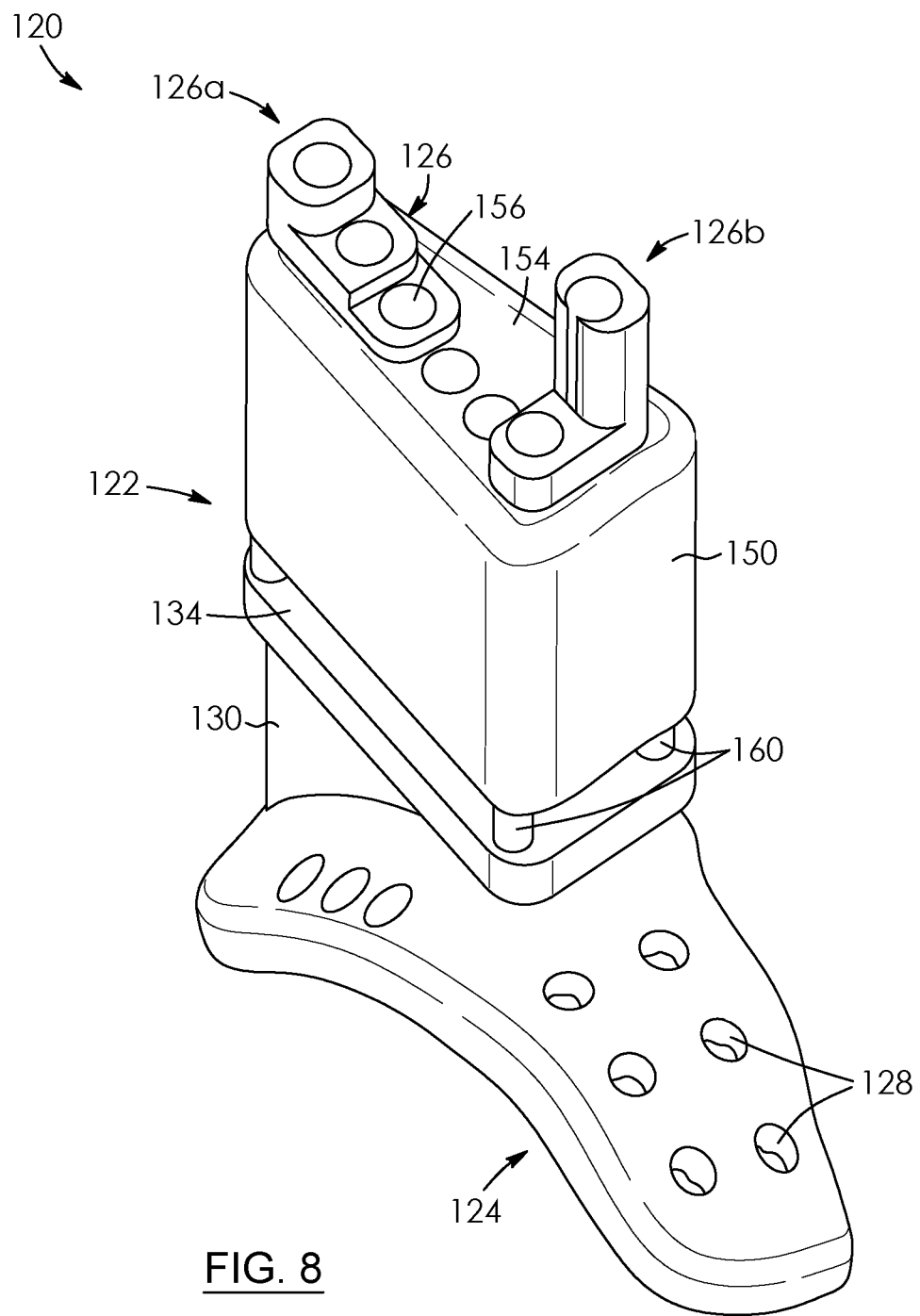
FIG. 8 is a perspective view of a unitary bone resection guide according to a second embodiment.

Now referring to FIG. 8, there is shown an alternative embodiment where the bone resection guide 120 is unitary, and in which likes features are numbered with corresponding reference number in the 100 series.

The bone resection guide 120 also has a body 122 with a bone-facing surface 124 similar to the above described bone-facing surface 24. The body 122 of the bone resection guide 120 also comprises a resection alignment guide 126 extending therethrough and which defines at least one resection plane. The resection alignment guide 126 is once again configured for guiding at least one resection tool along the at least one resection plane as described above.

In the embodiment shown in FIG. 8, the bone resection guide 120 is unitary and therefore, the body 122 is a single piece component including the resecting section 130 with similar characteristics as the above described resecting section 30 and a drilling section 150 with similar characteristics as the above described drilling section 150, and which are permanently connected together to form a single piece. The resecting section 130 and the drilling section 150 are connected by at least one permanent connector 160, such as connecting pins, connected at one end to the extension engaging surface 134 of the resecting section 130 and at an opposed end to the connecting surface 152 (FIGS. 9 and 10) of the drilling section 150. As will be described in more details below, the at least one permanent connecting pins 160 can be severed or broken in order to disengage the resecting section 130 from the drilling section 150.

In the embodiment shown, similarly to the above-described embodiment, the resecting section 130 also includes a resecting slot 132 (as better seen in FIG. 11) similar to the above described resecting slot 32, and a fastening assembly 128, such as fastening apertures where fasteners can be inserted to secure the resecting section 130 to the bone of the patient. Also similarly as the above-described embodiment, the drilling section 150 also includes a plurality of guiding bores 156 defining the resection alignment guide 126 together with the resecting slot 132. The plurality of guiding bores 156 extend between the tool engaging surface 154 and the connecting surface 152. Once again the length of each one of the guiding bores 156 is variable, as a result of a variation of the thickness of sections of the drilling section 150.

In another alternative (not shown), the resecting section 130 can be free of resecting slot 132 but rather include a plurality of bores aligned, or in register, with the plurality of guiding bores 156 of the drilling section 150. In such an embodiment, the alignment guide 126 includes the plurality of guiding bores 156 of the drilling section 150 and the corresponding plurality of bores of the resecting section 130. Moreover, one skilled in the art will understand that, in an embodiment, the resecting section 130 and the drilling section 150 can be merged into a single section, rather than being permanently connected to one another, with guiding bores extending therethrough, between the tool engaging surface 154 and the bone-facing surface 124.

Figure 9:
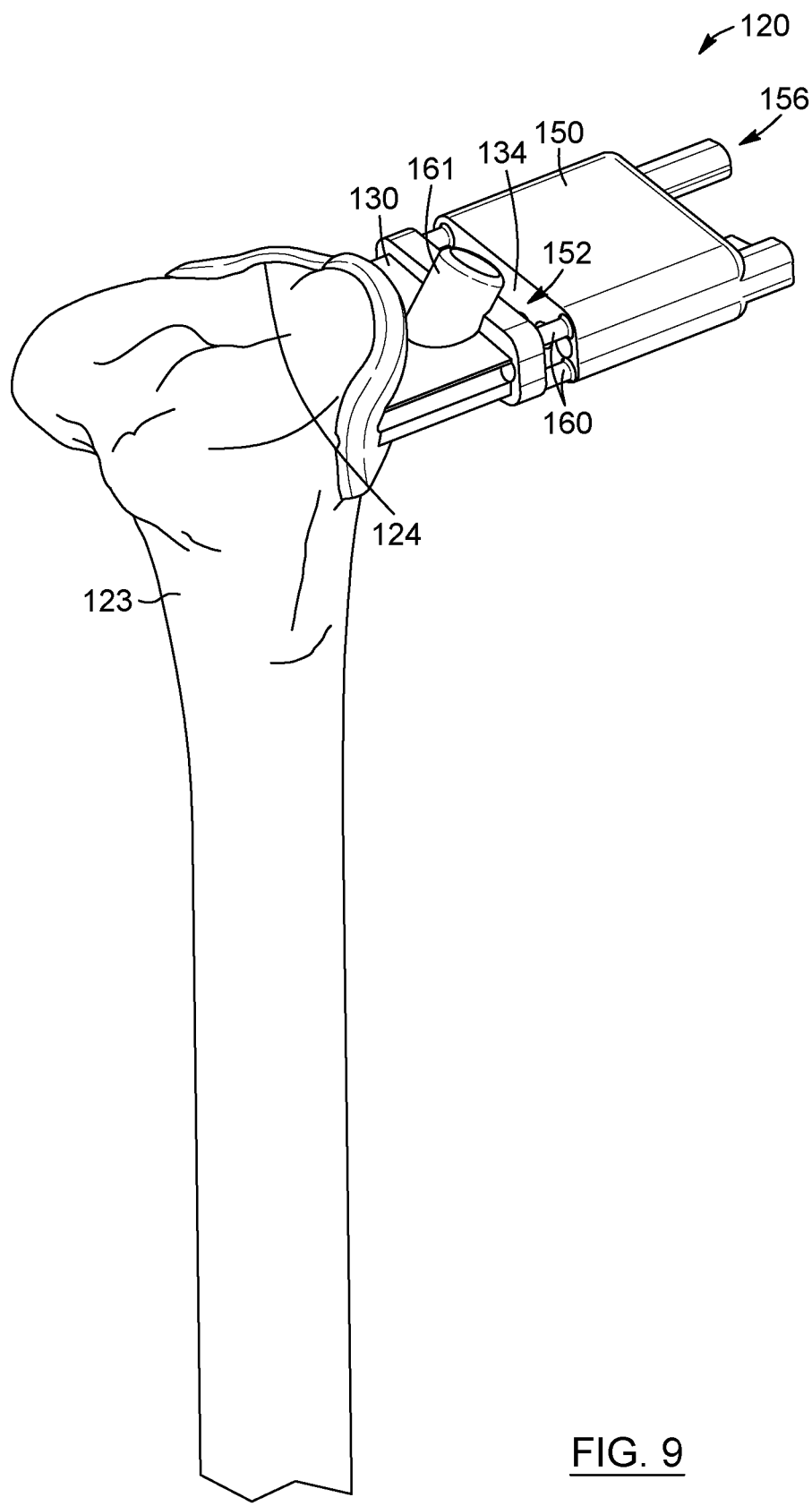
FIG. 9 is a perspective view of the unitary bone resection guide of FIG. 8 secured to a tibia.

In the embodiment shown in FIGS. 8 and 9, the resecting section 130 also includes a hose connector 161 defining a fluid channel extending between a bone facing surface port at a proximal end and opening on the bone facing surface 124 and a hose receiving port at a distal end and configured to connect a hose (not shown) thereto. The hose connector 161 therefore allows an injection of fluid, such as water, from the hose, at the bone facing surface 124, during the resection of the portion of the bone 123, as will be described in more details below. One skilled in the art will understand that, in an embodiment, the bone resection guide 20 according to other alternative embodiments, such as the above described embodiment shown in FIGS. 1 to 3 can also be provided with a hose connector 161.

Once again, the unitary bone resection guide 120 can be made of any biocompatible material, such as metal, plastic, polymer, composite materials or the like. Each bone resection guide 120 can be manufactured by known machining methods such as, without being limitative, stereolithography methods, selective laser sintering, fused deposition modeling, milling, injection molding or the like.

One skilled in the art will understand that several alternative embodiments can be foreseen to the bone resection guide 20 and 120 described above and shown in the attached figures. For instance and without being limitative, the non-unitary bone resection guide 20 can include more than two detachably engageable sections, the drilling section can include two connectable sections configured to permanently engage the fastener 59 therewith, the resecting section 30, 130 and the drilling section 50, 150 can be merged into a single section, or the like.

Referring now to FIGS. 4 to 7 and 9 to 12d, a sequence of operation for performing the resection of a portion of a bone of a patient, using the above described bone resection guide 20, 120, according to an embodiment, will now be described. As mentioned above, the method associated to the bone resection guide 20, 120 will be described in reference to a tibia resection. However, one skilled in the art will readily understand that the method described below can be applied to resect other bones than a tibia.

In an embodiment, in a preoperative stage, an image of at least a portion of the patient bone 23, 123 on which the resection is to be performed is obtained. The image can be obtained using known imaging techniques, such as, without being limitative, magnetic resonance imaging (MRI), computed axial tomography (CAT scan), ultrasound, X-ray, or the like and various CAD software for the three-dimensional image reconstruction. The image obtained is subsequently used to generate a computer model of the at least a portion of the patient bone 23, 123. As previously mentioned, in the illustrated embodiment, the bone 23, 123 to be resected is a tibia, for example and without being limitative for a unicompartemental knee arthroplasty.

Once the image of at least a portion of the patient bone 23, 123 has been obtained, the patient-specific bone resection guide 20, 120 is designed and conceived. As described above, the bone-facing surface 24, 124 of the resecting section 30, 130 is designed to conform precisely to the contour of the portion of the bone 23, 123 onto which the resection guide 20, 120 is to be detachably secured. As previously mentioned, in an embodiment, the bone-facing surface 24, 124 is textured with protrusions and corresponding channels therebetween in order to allow the proper placement of the resecting section 30, 130 on the corresponding portion of the bone surface of the patient, even if a quantity of soft tissues remains on the bone.

The resection alignment guide 26, 126 of the bone resection guide 20, 120 is also conceived and designed for guiding the at least one resection tool to perform the specific preoperatively predetermined resection of the bone, 23, 123. Therefore, in an embodiment, in order to conceive and design the bone resection guide 20, 120, a bone resection path is determined and the resection alignment guide 26, 126 is aligned with the bone resection path. The conception and the design of the bone resection guide 20, 120 are carried out with specialized software using a computer model of the portion of the patient bone 23, 123 generated from the images obtained at the imaging step. Then, the bone resection guide 20 is manufactured based on a model conceived with the specialized software.

Referring to FIGS. 4, 5, 7, 9 and 10, in the operative stage, the bone resection guide 20, 120 is positioned on a predetermined surface of the bone 23, 123 of the patient in a predetermined configuration, corresponding to the bone-facing surface 24, 124, and is secured thereto. In an embodiment, the bone resection guide 20, 120 is secured to the bone 23, 123 using known fasteners such as screws engaged in both the bone and the bone resection guide 20, 120 and, more particularly, the resecting section 30, 130.

Figure 4:
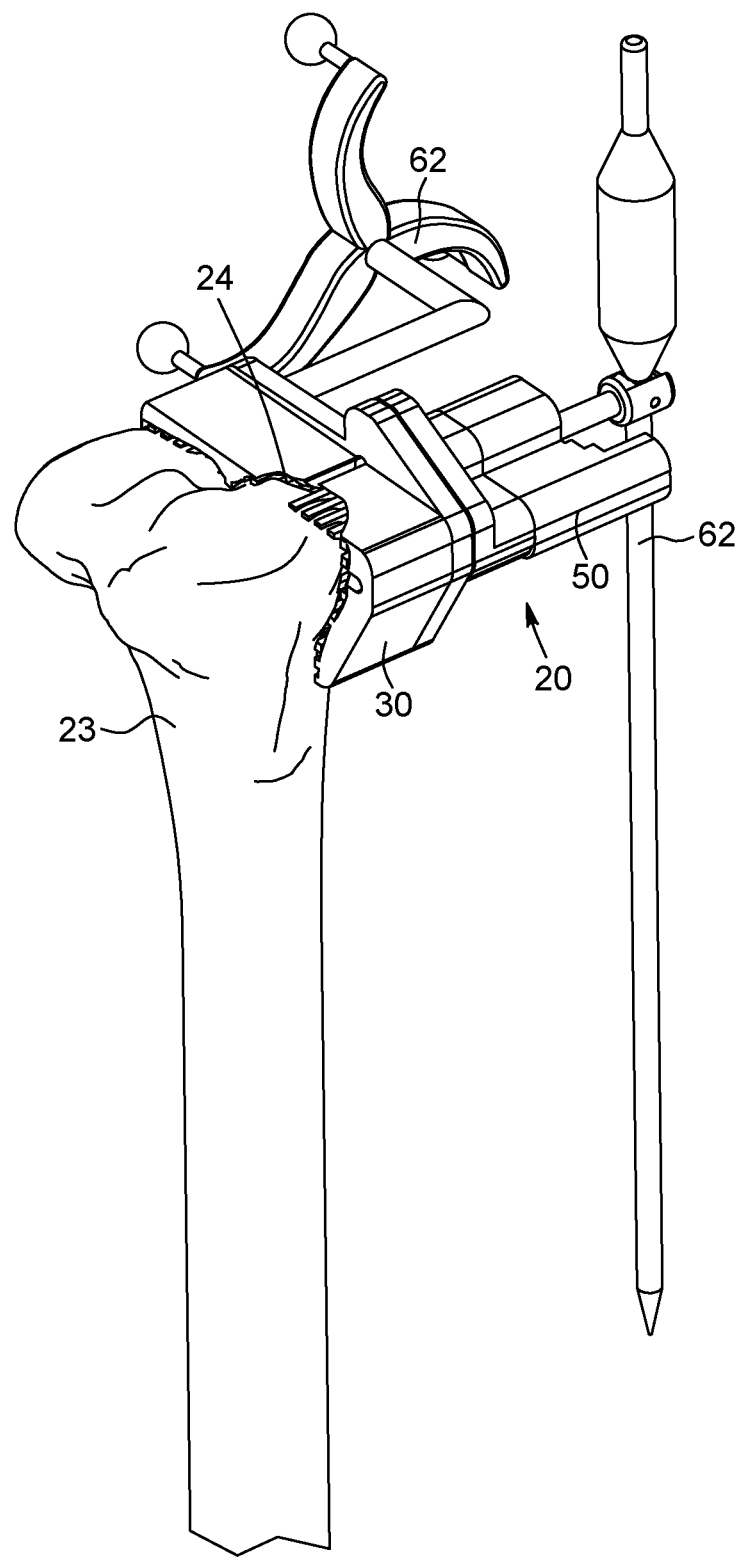
FIG. 4 is a perspective view of the non-unitary bone resection guide of FIG. 1 secured to a tibia and with validation components mounted thereto.
Figure 5:
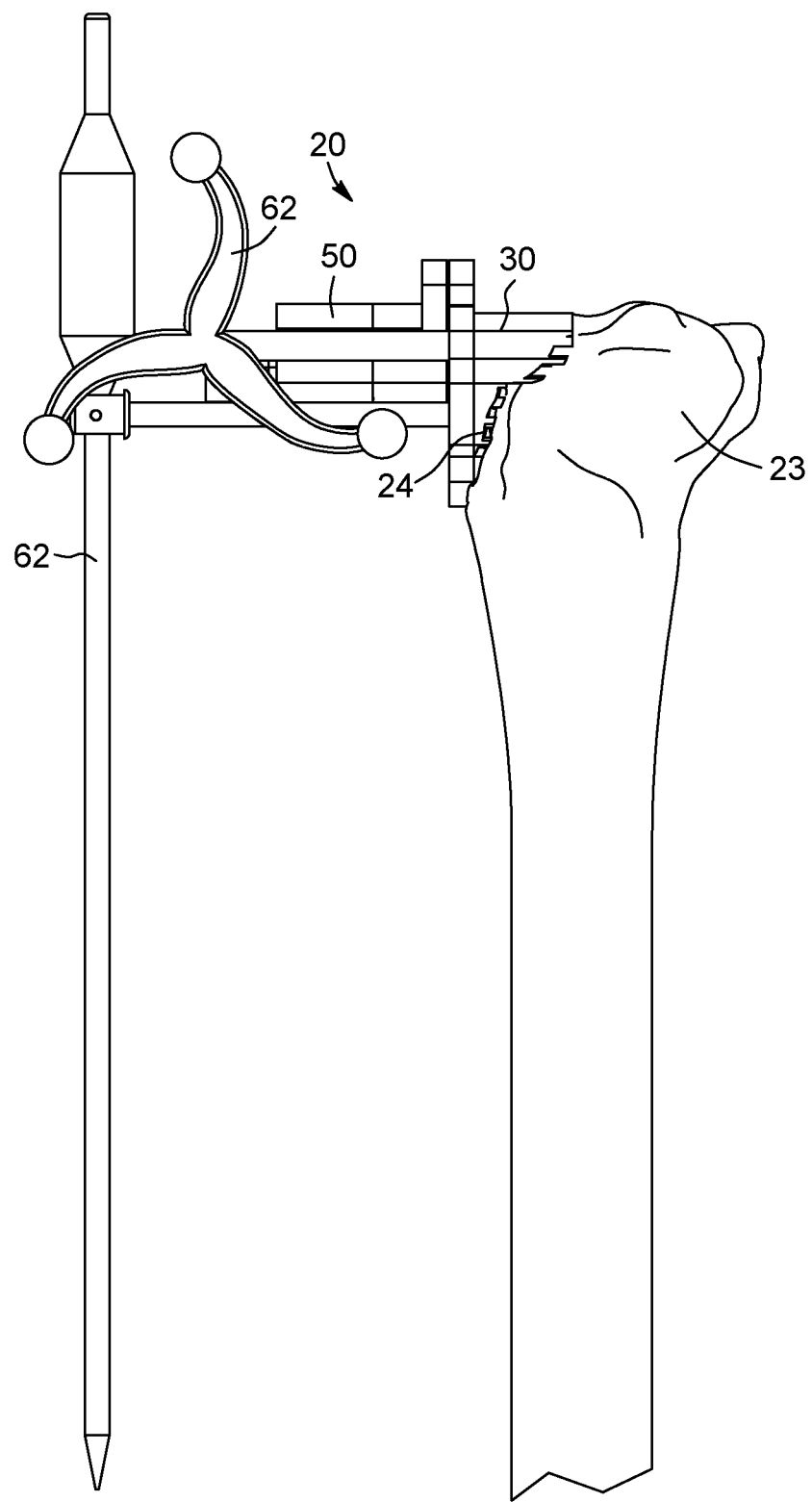
FIG. 5 is a side elevation view of the non-unitary bone resection guide and validation components of FIG. 4 secured to a tibia.
Figure 7:
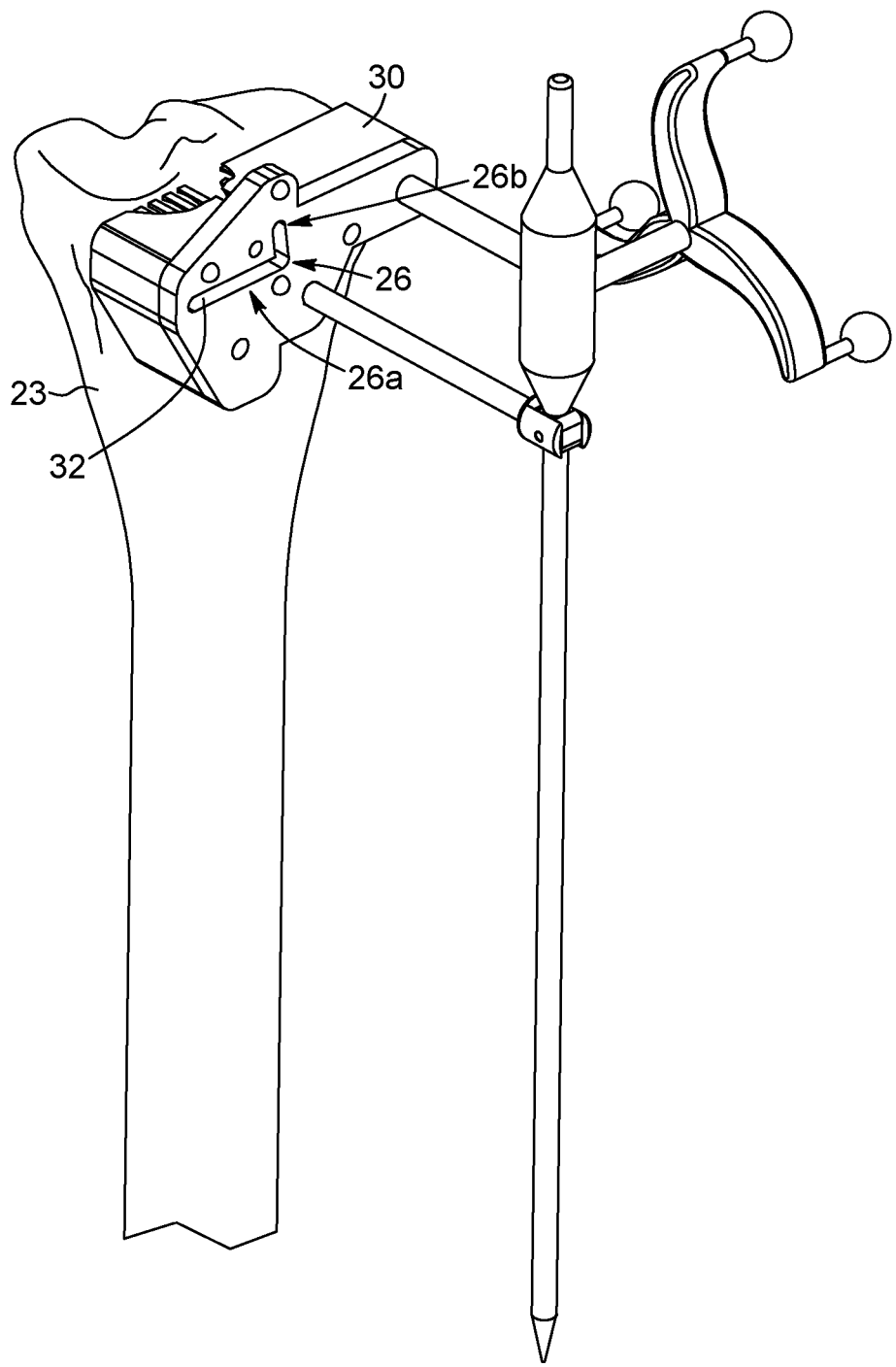
FIG. 7 is a perspective view of the non-unitary bone resection guide and validation components of FIG. 4, shown in a cutting configuration where the drilling section has been removed.

In the case of the non-unitary bone resection guide 20, with reference to FIGS. 4, 5 and 7, in an embodiment, the bone resection guide 20 is positioned and secured to the portion of the bone 23 with the resecting section 30 and the drilling section 50 engaged together. In an alternative embodiment, the resecting section 30 can firstly be positioned on the bone 23 and be secured thereto. Such an intermediary step is shown in FIG. 7. Once the resecting section 30 has been secured to the bone 23, the drilling section 50 can subsequently be secured to the resecting section 30, without being secured to the bone itself.

As can be seen in FIGS. 4 to 7, several conventional validation instruments 62 can be mounted onto the non-unitary resection guide 20 to assist the surgeon in validating the positioning of the resection guide 20 and the corresponding position of the resection alignment guide 26. The conventional validation instruments 62 can be mounted to the bone resection guide 20 with or without the drilling section 50 mounted to the resecting section 30.

Figure 10:
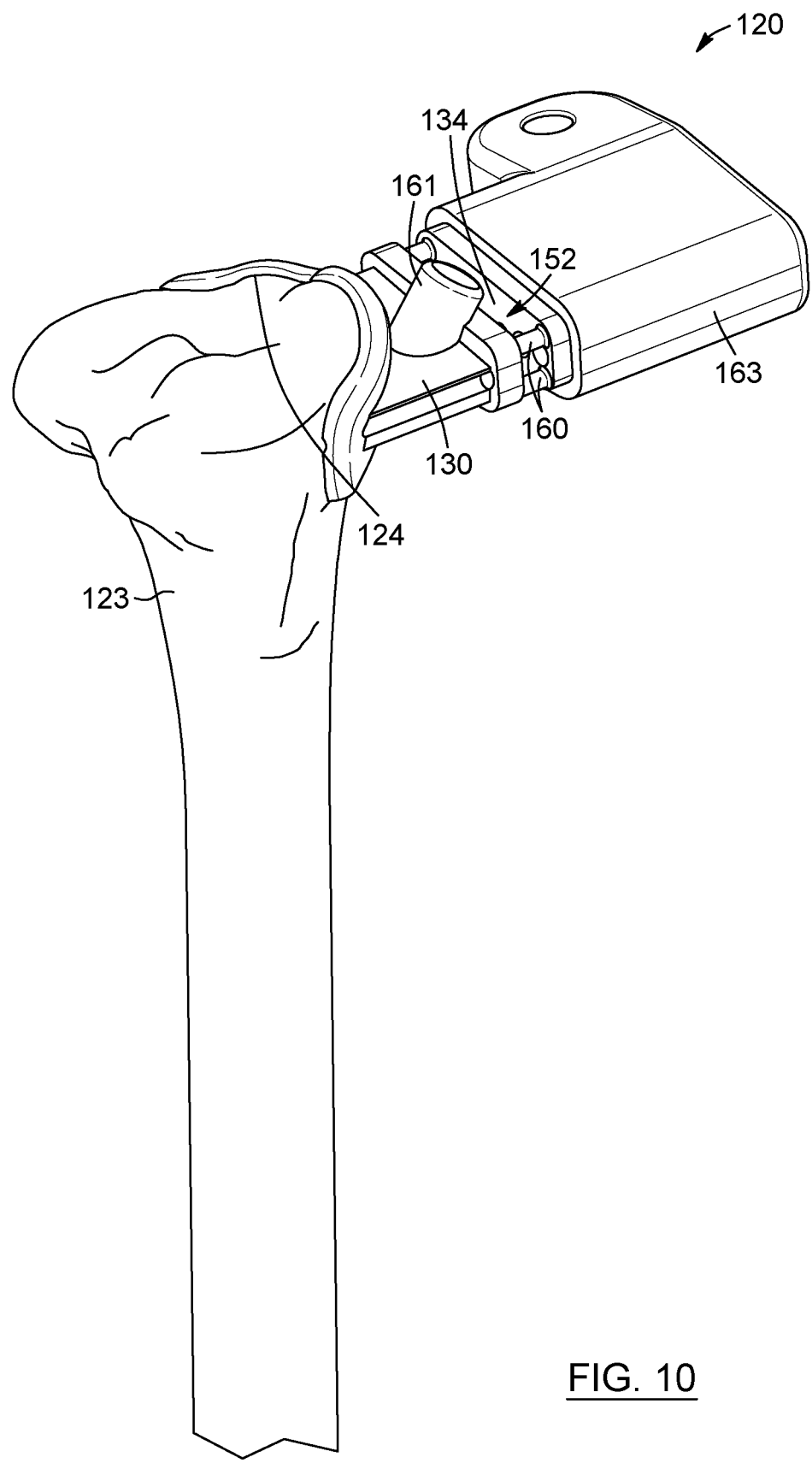
FIG. 10 is a perspective view of the unitary bone resection guide of FIG. 8 secured to a tibia, and shown with a validation component mounting cap mounted thereto.

Referring to FIG. 10, in an embodiment, conventional validation instruments (not shown) can be mounted onto the bone resection guide 120 by way of a validation component mounting cap 163 removably slidable over the drilling section 150 of the bone resection guide 120 and configured to secure validation instruments thereto in order to assist the surgeon in validating the positioning of the resection guide 120 and the corresponding position of the resection alignment guide 126 thereof. One skilled in the art will understand that, in alternative embodiments, the validation component mounting cap 163 can also engage the bone resection guide 120 differently than by sliding over the drilling section 150 of the bone resection guide 120 as in the embodiment shown. Moreover, One skilled in the art will understand that, in an embodiment (not shown), the unitary bone resection guide 120 can be configured to allow the conventional validation instruments 62 to be mounted thereto, without using the validation component mounting cap 163.

Referring back to FIGS. 4, 5, 7, 9 and 10, once the bone resection guide 20, 120 has been secured to the bone 23, 123 and the positioning has been validated, the resection of the portion of the bone 23, 123 can be performed. As mentioned above, in the illustrated embodiment, the resection alignment guide 26, 126 is configured to perform a medial resection of a tibial bone. A substantially horizontal resection plane 26a, 126a is defined to perform a substantially horizontal resection and a substantially vertical resection plane 26b, 126b is configured to perform a substantially vertical resection of the bone 23, 123. Using the resection guide 20, 120 described above, the resection of the portion of the bone 23, 123 is performed in two steps: a first weakening step and a subsequent resection step.

Figure 6:
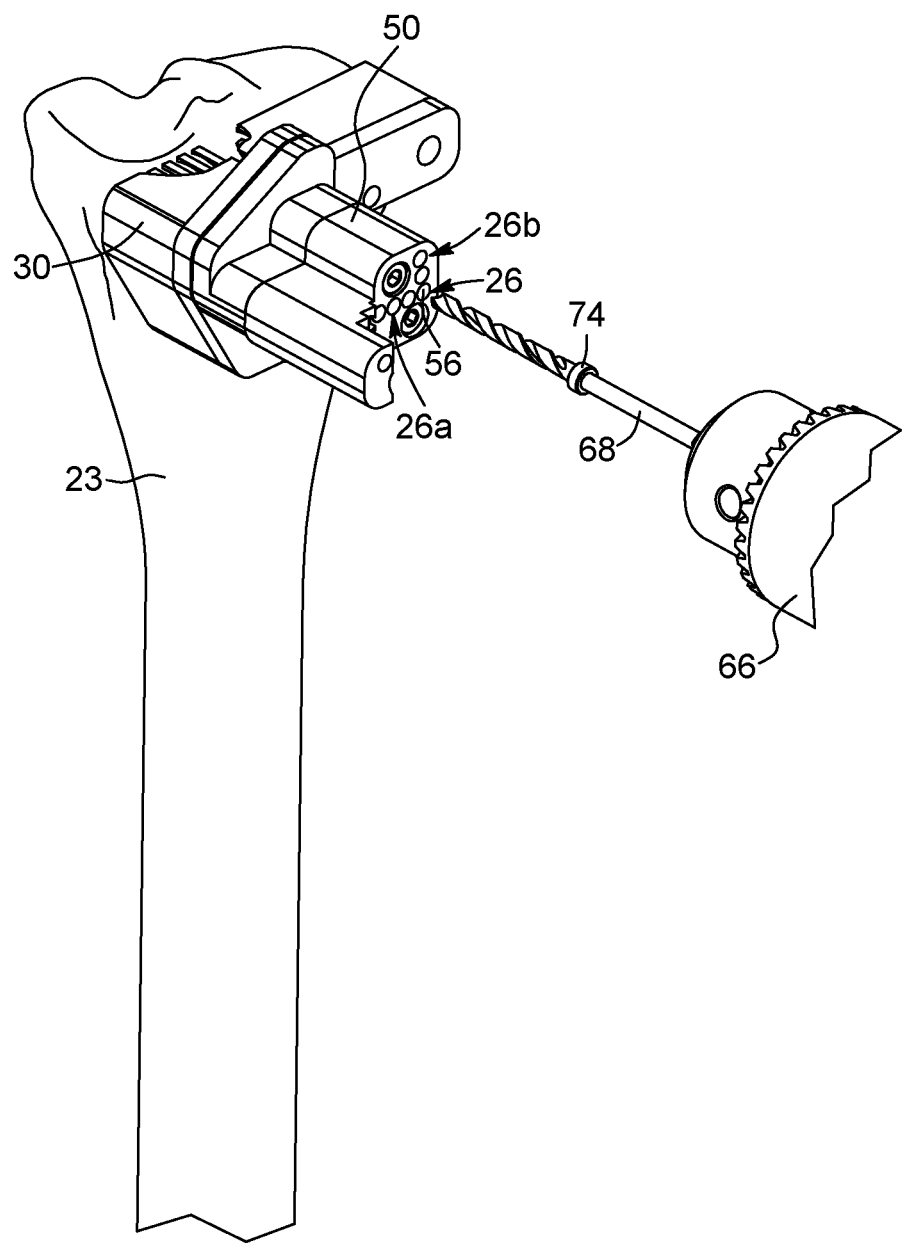
FIG. 6 is a perspective view of the non-unitary bone resection guide of FIG. 4 secured to a tibia and in combination with a drilling tool.
Figure 12A:
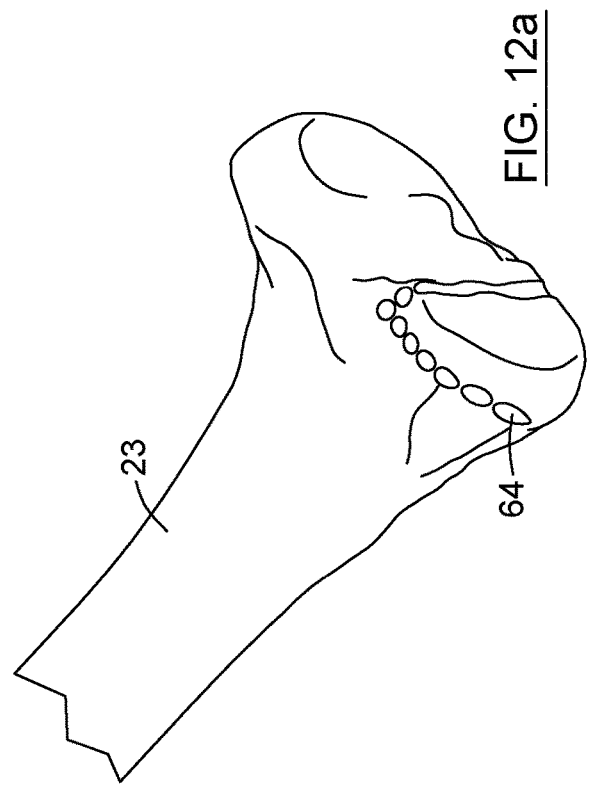
FIGS. 12a to 12d are schematic representations of the different stages of a resection of a tibia according to an embodiment of a resection method.

As can be better seen in FIGS. 6, 9 and 12a, in the weakening step, the bone 23, 123 of the patient is weakened by drilling a plurality of holes 64 therein, each hole corresponding to one of the guiding bores 56, 156. The plurality of holes 64 are drilled using a drilling instrument 66 of the resection tools, with a drilling member 68 insertable into each one of the plurality of guiding bores 56, 156 of the drilling section 50. The holes 64 follow at least one plane previously defined in the preoperatively predetermined resection of the bone 23, 123. In FIG. 12a, the preoperatively predetermined resection is a medial resection of the tibial bone 23. The holes 64 follow a substantially horizontal plane defined by the substantially horizontal resection plane 26a of the resection alignment guide 26, 126 and a substantially vertical plane defined by the substantially vertical resection plane 26b of the resection alignment guide 26, 126.

In an embodiment, the thickness of the drilling section 50, 150 is configured such that an insertion of the drilling member 68 into each one of the guiding bores 56, 156 forms a hole 64 in the bone 23, 123 which substantially extends between an anterior surface and a posterior surface of the bone 23, 123. In other words, the thickness of the drilling section 50, 150 varies according to the depth of each one of the holes 64 to be drilled through the bone. The drilling section 50 is thicker in sections of the bone where shorter holes must be performed while the drilling section 50 is thinner in sections of the bone where longer holes must be performed.

As can be seen in FIG. 6, in an embodiment, the drilling member 68 includes a blocking sleeve 74 preventing the drilling member from traveling further into each one of the guiding bores 56 once a predetermined fixed length has been inserted therein. The control of the depth of each one of the holes 64 to be drilled through the bone therefore results from the combination of the position of the blocking sleeve 74 on the drilling member 68 and the variable thickness of the drilling section 50.

One skilled in the art will understand that, in an embodiment, the blocking sleeve 74 can be integral to the drilling member 68. In such an embodiment, drilling members 68 of different fixed lengths between a tip and the blocking sleeve 74 can be provided. It will be understood that the drilling member 68 can also be patient specific, the position of the blocking sleeve 74 being adapted to a particular patient. In an alternative embodiment, the blocking sleeve 74 can be removably connected to the drilling member 68. In such an embodiment the position of the blocking sleeve 74 can be adjustable, for example and without being limitative, using a set screw assembly. In view of the above, one skilled in the art will understand that the length of the drilling member 68, between its tip and the blocking sleeve 74 can differ from the one illustrated in FIG. 6.

Once the weakening step has been performed and the bone 23, 123 has been weakened along the at least one plane where resection is to be performed, the resection step can be performed. In a first embodiment the resection step is performed by disengaging the bone resection guide from the bone 23, 123 to allow access to the weakened section and performing manual resection of the portion of the bone. For example and without being limitative, the manual resection of the bone can be performed by the surgeon using a chisel, a manual bone saw, a bone rongeur, a bone cutter, or the like, along the weakened at least one resection plan where resection is required.

Figure 12B:
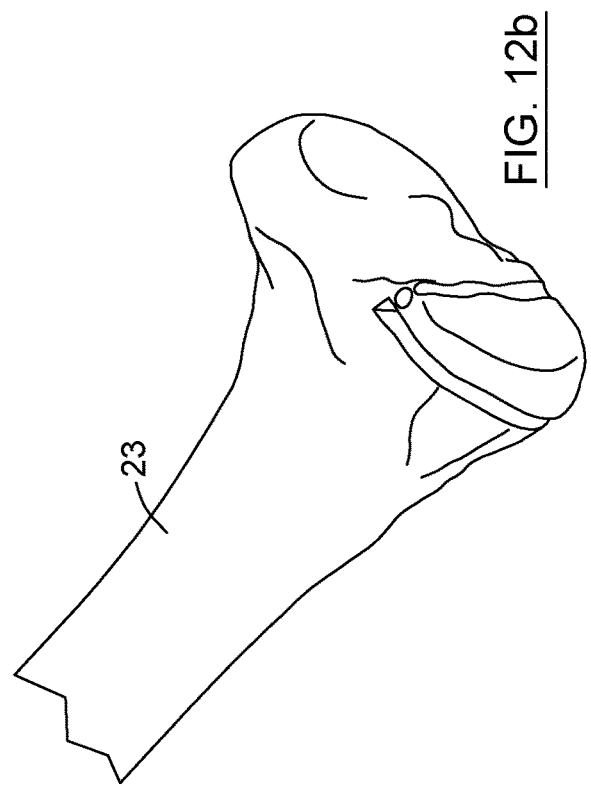
Figure 12C:
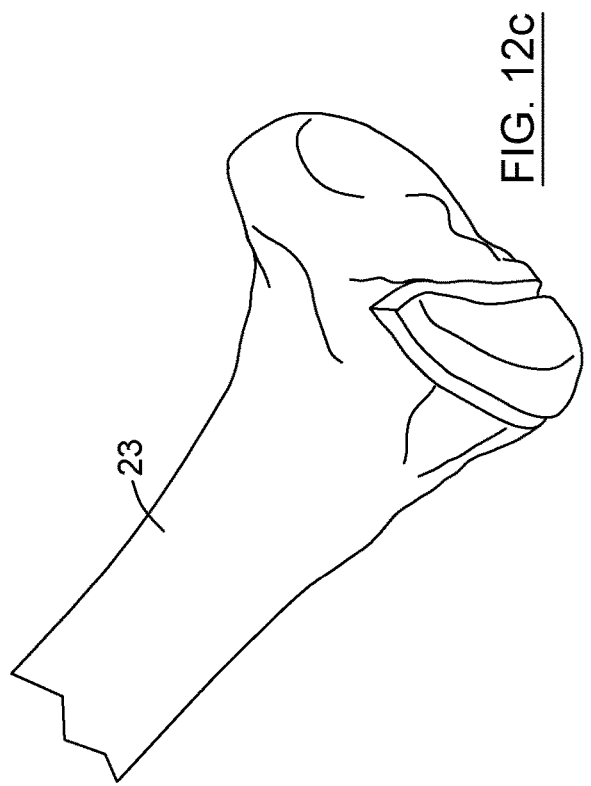
Figure 12D:
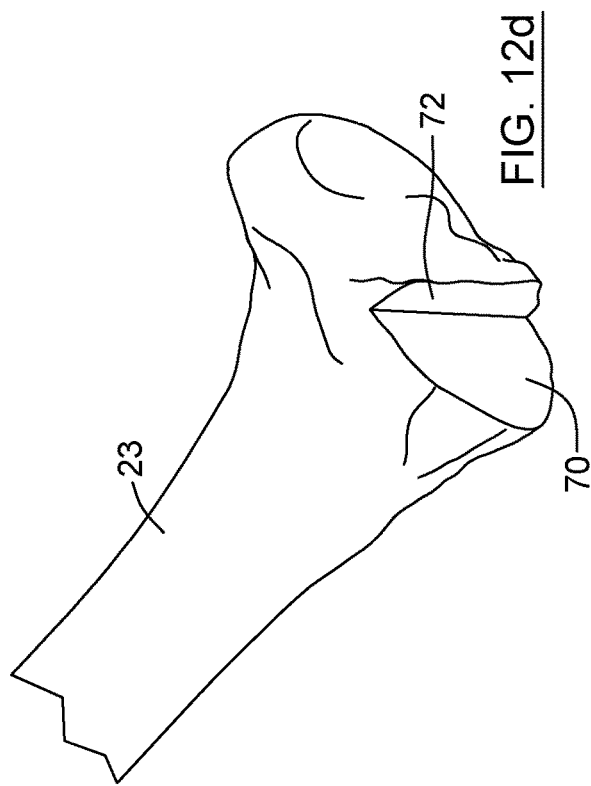

As better seen in FIGS. 12b to 12d, in the embodiment shown, during the resection step, the bone 23 is resected along the substantially horizontal plane (FIG. 12b) and the substantially vertical plane (FIG. 12c) previously weakened during the weakening step, in order to resect the desired bone portion. In the illustrated embodiment, the resection creates a medial plateau 70 and a medial substantially vertical wall 72 in the tibial bone 23. As mentioned above, in an embodiment, the angle between the medial plateau 70 and the medial vertical wall 72 is an acute angle. However, one skilled in the art will understand that different angles can be provided therebetween. The shape of the resected bone is complementary to the prothesis to be mounted to the bone.

In an alternative and non-limitative embodiment, the resecting slot 32, 132 of the resecting section 30, 130 is configured to guide a cutting tool to perform the predetermined resection.

Figure 11:
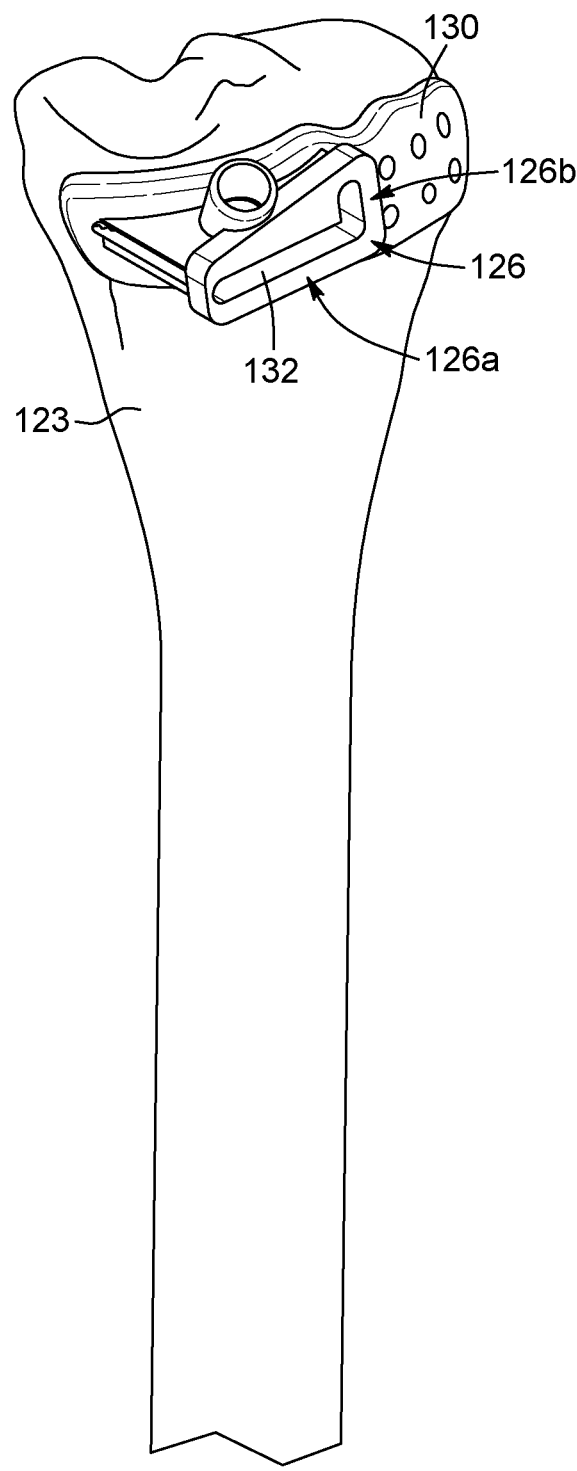
FIG. 11 is a perspective view of the unitary bone resection guide of FIG. 8, shown in a cutting configuration where the drilling section has been removed.

In order to proceed with the cutting step, the bone resection guide 20, 120 must be configured in a cutting configuration where the resecting slot 32, 132 is exposed and is unimpeded by the guiding bores 56. Such a cutting configuration is shown in FIGS. 7 and 11. In an embodiment, the cutting configuration is reached by detaching and removing the drilling section 50 from the resecting section 30 to expose the resecting slot 32 of the resecting section 30. In the embodiment shown in FIG. 7, removal of the drilling section 50 can be performed by unfastening the fastener removably maintaining the drilling section 50 and the resecting section 30 to disengage the sections from one another. In the embodiment shown in FIG. 11, removal of the drilling section 150 can be performed by cutting the connecting pins 160 permanently connecting the drilling section 150 and the resecting section 130 to disengage the sections from one another.

Once the drilling section 50, 150 has been removed, the cutting can be performed by passing a cutting blade (not shown) of a cutting tool (not shown), or any other suitable cutting tool, in the resecting slot 32, 132 of the resecting section 30, 130 and displacing the cutting tool such that the cutting blade is moved along the resecting slot 32, 132. One skilled in the art will understand that, in order to perform the cutting, the cutting tool must be configured in a cutting state, i.e. in an operative state where the cutting tool can perform cutting. The resecting slot 32, 132 defines a cutting path to be followed by the cutting tool. Given that, as mentioned above, the guiding bores 56, 156 used for weakening the bone 23, 123 in the weakening step were aligned with the resecting slot 32, 132, the cutting is performed along the same planes as the previous weakening.

One skilled in the art will understand that, the above described method for performing a resection of a bone can be used for performing other types of resections than the medial tibial resection illustrated in the appended figures. For example and without being limitative, it can be used to perform a lateral tibial resection, a femoral resection, or the like.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

What is claimed is:

1. A bone resection guide comprising:
a resecting section having a bone-facing surface with a bone-contacting section removably superposable against an at least partially unresected portion of a bone of a patient and nestingly conforming thereto, the resecting section further comprising at least one resecting slot extending therethrough to define a resection path; and
a drilling section comprising a plurality of guiding bores extending therethrough, the plurality of guiding bores being characterized by a plurality of different depths, the drilling section being engageable with the resecting section in a configuration wherein the plurality of guiding bores are aligned with the at least one resecting slot to define a resection alignment guide and a combined depth of the plurality of guiding bores and the at least one resecting slot is variable along the resection path when the drilling section and the resecting section are engaged together.

2. The bone resection guide as claimed in claim 1, wherein at least one of the resecting section and the drilling section comprises a section fastening assembly to detachably secure the resecting section and the drilling section together.

3. The bone resection guide as claimed in claim 2, wherein the section fastening assembly remains engaged with the at least one of the resecting section and the drilling section when the resecting section and the drilling section are disengaged from one another.

4. The bone resection guide as claimed in claim 1, wherein the resecting section and the drilling section are engageable together in a single configuration.

5. The bone resection guide of claim 1, wherein the at least one resecting slot is configured to create a bone resection along at least two resection planes.

6. The bone resection guide of claim 1, wherein the bone resection guide is configured for removal of a bone block from a bone of a patient and the resection path is configured to at least partially delimit the bone block to be removed from the bone of the patient, the bone block having a surface conforming substantially in shape to the at least one resection plane.

7. The bone resection guide of claim 1, wherein the combined depth of the drilling and resecting sections is variable according to a depth of a section of the bone to be resected, the combined depth being thicker for a shorter bone resection and thinner for a longer bone resection.

8. The bone resection guide of claim 1, wherein the drilling section comprises a connecting face and a tool engaging face and the resecting section comprises an extension engaging surface, the connecting face of the drilling section being superposed to the extension engaging surface of the resecting section when the drilling and resecting sections are engaged and secured together, and wherein the at least one resecting slot extends between the bone-facing surface and the extension engaging surface and the plurality of guiding bores extends between the connecting face and the tool engaging face.

9. The bone resection guide of claim 1, wherein the bone-facing surface of the resecting section has a greater surface area than the bone-contacting section thereof.

10. The bone resection guide of claim 1, wherein the at least one resecting slot extends at least to a profile edge of the bone at at least one end thereof to be capable of performing a bone cut opened on an unresected portion of a bone surface.

11. The bone resection guide of claim 1, wherein the at least one resecting slot extends at least to a profile edge of the bone at at least one end thereof to be capable of performing a bone cut opened at the profile edge.

12. The bone resection guide of claim 1, wherein the resecting section comprises a bone fastening assembly to removably secure the resecting section to the bone of the patient.

13. The bone resection guide of claim 1, wherein a plurality of the plurality of guiding bores have a section extending outwardly of the at least one resecting slot when the resecting section and the drilling section are engaged together and a plurality of the sections of the guiding bores that extend outwardly of the at least one resecting slot have a plurality of different depths.

14. The bone resection guide of claim 1, further comprising at least one permanent connector extending between the resecting section and the drilling section when secured together, the at least one permanent connector being severable to disengage the drilling section from the resecting section and expose the at least one resecting slot.

15. A bone resection guide comprising:
a resecting section having a bone-facing surface and an extension engaging surface, the extension engaging surface being opposed to the bone-facing surface, the resecting section further comprising at least one resecting slot extending therethrough between the bone-facing surface and the extension engaging surface and defining a resection path to create a bone resection along at least one resection plane; and
a drilling section having a connecting surface and a tool engaging surface, the tool engaging surface being opposed to the connecting surface, the drilling section comprising a plurality of guiding bores extending therethrough from the tool engaging surface to the connecting surface, the drilling section being engageable with the resecting section with the connecting surface of the drilling section facing the extension engaging surface of the resecting section with the plurality of guiding bores being aligned with the at least one resecting slot, wherein at least two adjacent ones of the plurality of guiding bores have a variable depth and the plurality of guiding bores and the at least one resecting slot define a resection alignment guide having a variable depth along the resection path.

16. The bone resection guide as claimed in claim 15, wherein the bone-facing surface comprises a bone-contacting section removably superposable against an at least partially unresected portion of a bone of a patient and nestingly conforming thereto.

17. The bone resection guide as claimed in claim 15, wherein at least one of the resecting section and the drilling section comprises a section fastening assembly to detachably secure the resecting section and the drilling section together and the section fastening assembly remains engaged with the at least one of the resecting section and the drilling section when the resecting section and the drilling section are disengaged from one another.

18. The bone resection guide of claim 15, wherein the bone resection guide is configured for removal of a bone block from a bone of a patient and the resection path is configured to at least partially delimit the bone block to be removed from the bone of the patient, the bone block having a surface conforming substantially in shape to the at least one resection plane.

19. The bone resection guide of claim 15, wherein a combined depth of the drilling and resecting sections when secured together is variable according to a depth of a section of the bone to be resected, the combined depth being thicker for a shorter bone resection and thinner for a longer bone resection.

20. The bone resection guide of claim 15, wherein the at least one resecting slot extends at least to a profile edge of the bone at at least one end thereof to be capable of performing a bone cut opened on an unresected portion of a bone surface.

21. The bone resection guide of claim 15, wherein a plurality of the plurality of guiding bores have a section extending outwardly of the at least one resecting slot when the resecting section and the drilling section are engaged together and a plurality of the sections of the guiding bores that extend outwardly of the at least one resecting slot have a plurality of different depths.

22. The bone resection guide of claim 15, further comprising at least one permanent connector extending between the resecting section and the drilling section when secured together, the at least one permanent connector being severable to disengage the drilling section from the resecting section and expose the at least one resecting slot.

23. A bone resection guide comprising:
a resecting section having a bone-facing surface and at least one resecting slot extending therethrough and defining a resection path, the bone-facing surface comprises a bone-contacting section removably superposable against an at least partially unresected portion of a bone of a patient and nestingly conforming thereto; and
a drilling section comprising a plurality of guiding bores extending therethrough and being engageable with the resecting section in a configuration wherein the plurality of guiding bores are aligned with the at least one resecting slot, the plurality of guiding bores being characterized by a plurality of different depths extending outwardly of the at least one resecting slot when the resecting section and the drilling section are engaged together.

24. The bone resection guide of claim 23, further comprising at least one permanent connector extending between the resecting section and the drilling section when secured together, the at least one permanent connector being severable to disengage the drilling section from the resecting section and expose the at least one resecting slot.

25. The bone resection guide of claim 23, wherein the drilling section is detachably mountable to the resecting section and at least one of the resecting section and the drilling section comprises a section fastening assembly to detachably secure the resecting section and the drilling section together in a single configuration.

26. The bone resection guide of claim 23, wherein a combined depth of the drilling and resecting sections when secured together is variable according to a depth of a section of the bone to be resected, the combined depth being thicker for a shorter bone resection and thinner for a longer bone resection.

27. The bone resection guide of claim 23, wherein the plurality of guiding bores have a variable depth along the resection path.

28. The bone resection guide of claim 23, wherein the bone-facing surface of the resecting section has a greater surface area than the bone-contacting section thereof and the at least one resecting slot extends at least to a profile edge of the bone at at least one end thereof to be capable of performing a bone cut opened on an unresected portion of a bone surface.

* * * * *